(12) United States Patent
Niemelä et al.

(10) Patent No.: US 9,791,361 B2
(45) Date of Patent: Oct. 17, 2017

(54) METHOD AND APPARATUS FOR MEASURING AEROSOL PARTICLES OF EXHAUST GAS

(71) Applicant: Dekati Oy, Kangasala (FI)

(72) Inventors: Ville Niemelä, Kangasala (FI); Leo Holma, Kangasala (FI); Sami Lundahl, Kangasala (FI); Tyler Beck, Vadnais Heights, MN (US)

(73) Assignee: Dekati Oy, Kangasala (FI)

( * ) Notice: Subject to any disclaimer, the term of this patent is extended or adjusted under 35 U.S.C. 154(b) by 240 days.

(21) Appl. No.: 14/922,626

(22) Filed: Oct. 26, 2015

(65) Prior Publication Data

US 2017/0115198 A1    Apr. 27, 2017

(51) Int. Cl.
| | |
|---|---|
| *G01N 15/06* | (2006.01) |
| *G01M 15/10* | (2006.01) |
| *G01N 15/00* | (2006.01) |

(52) U.S. Cl.
CPC ...... *G01N 15/0656* (2013.01); *G01M 15/102* (2013.01); *G01N 2015/0046* (2013.01)

(58) Field of Classification Search
CPC .................................. G01N 15/0656
See application file for complete search history.

(56) References Cited

U.S. PATENT DOCUMENTS

| | | |
|---|---|---|
| 3,114,877 A | 12/1963 | Dunham |
| 3,949,390 A | 4/1976 | Rayl et al. |
| 6,228,149 B1 | 5/2001 | Alenichev et al. |
| 6,502,450 B1 | 1/2003 | Patashnick et al. |
| 7,174,767 B2 | 2/2007 | Booker |
| 2006/0150754 A1 | 7/2006 | Burtscher et al. |
| 2011/0072786 A1 | 3/2011 | Tokuda et al. |
| 2011/0120096 A1 | 5/2011 | Nakamura |
| 2011/0220811 A1 | 9/2011 | Dick et al. |
| 2012/0180659 A1 | 7/2012 | Laitinen et al. |
| 2015/0192508 A1 | 7/2015 | Janka |

FOREIGN PATENT DOCUMENTS

| | | |
|---|---|---|
| DE | 4008348 A1 | 9/1991 |
| GB | 1335778 A | 10/1973 |
| JP | 2005091043 A | 4/2005 |
| WO | 2006127803 A2 | 11/2006 |
| WO | 2012022842 A1 | 2/2012 |
| WO | 2013132154 A1 | 9/2013 |

OTHER PUBLICATIONS

U.S. Office Non-Final Office Action, U.S. Appl. No. 14/922,599, dated Apr. 6, 2017, 28 pages.

(Continued)

*Primary Examiner* — Clayton E Laballe
*Assistant Examiner* — Dennis Hancock
(74) *Attorney, Agent, or Firm* — Ziegler IP Law Group, LLC

(57) ABSTRACT

A particle measuring apparatus includes a distributor unit arranged to provide a first partial flow and a second partial flow by separating the second partial flow from an input flow, a particle collecting unit to collect particles from the first partial flow by using a first filter, and a particle monitoring unit to form charged particles by charging particles carried by the second partial flow, and to provide an electric current by collecting the charged particles.

18 Claims, 19 Drawing Sheets

(56) References Cited

OTHER PUBLICATIONS

Office Action, Finnish Patent and Registration Office, Application No. 20155760, dated May 20, 2016, 7 pages.
International Search Report, Application No. PCT/FI2016/050684, dated Jan. 5, 2017, 5 pages.
Written Opinion of the International Searching Authority, Application No. PCT/FI2016/050684, dated Jan. 5, 2017, 8 pages.
H. Burtscher, "Physical characterization of particulate emissions from diesel engines: A review", Journal of Aerosol Science. vol. 36. No. 7 2005, Received Jun. 29, 2004; received in revised form Dec. 7, 2004, 37 pages.
Wayne Ott et al., "Using multiple continuous fine particle monitors to characterize tobacco, incense, candle, cooking, wood burning, and vehicular sources in indoor, outdoor, and in-transit settings." Atmospheric Environment. vol. 40. No. 5, 2006. Received Sep. 20, 2004; received in revised form Aug. 11, 2005; accepted Aug. 11, 2005, 23 pages.
International Search Report, Application No. PCT/FI2016/050685, dated Dec. 19, 2016, 5 pages.
Written Opinion of the International Searching Authority, Application No. PCT/FI2016/050685, dated Dec. 19, 2016, 9 pages.
International Search Report, Application No. PCT/FI2016/050686, dated Dec. 21, 2016, 5 pages.
Written Opinion of the International Searching Authority, Application No. PCT/FI2016/050686, dated Dec. 21, 2016, 9 pages.

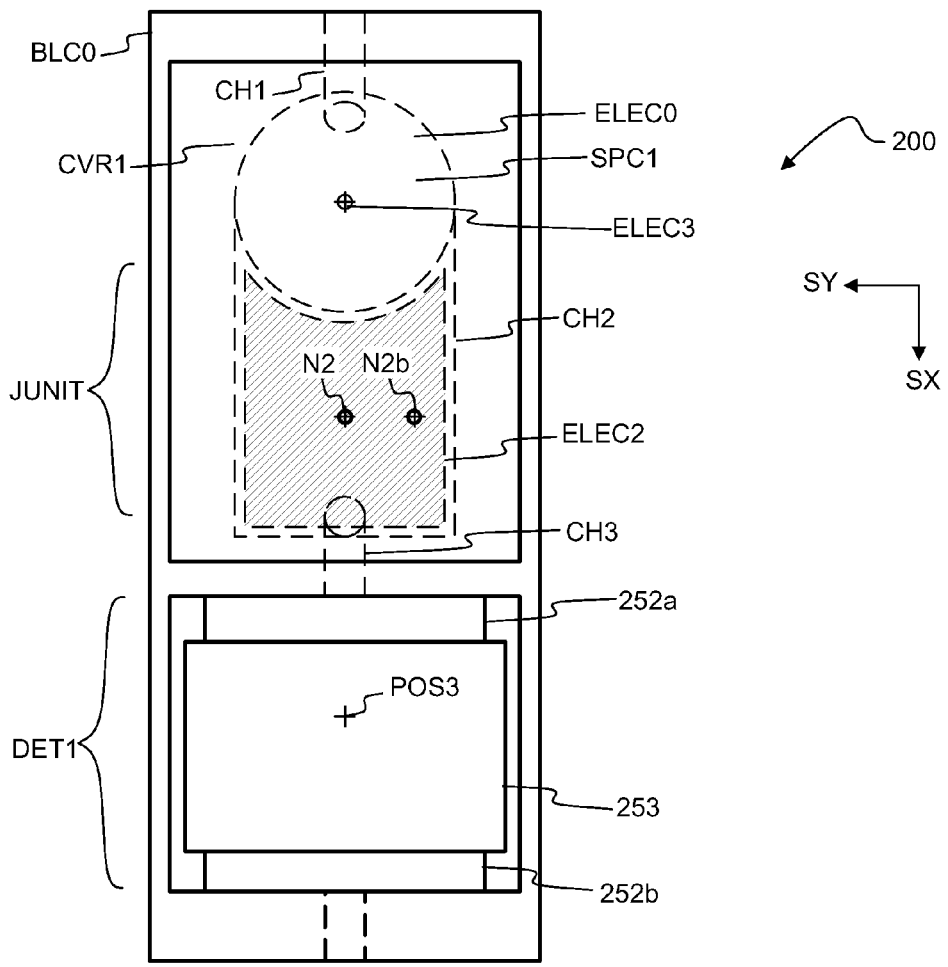
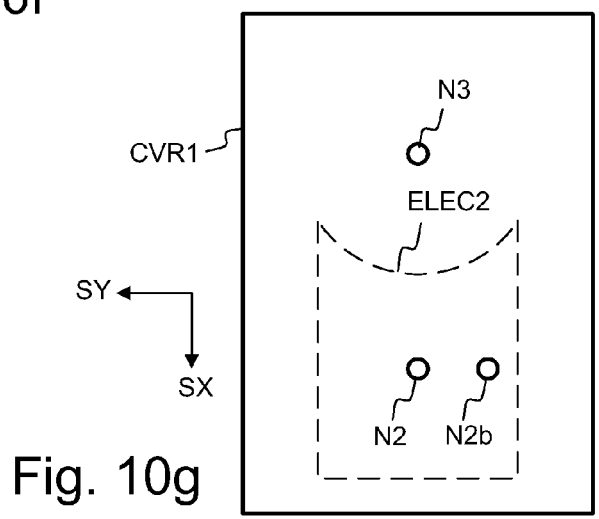
Fig. 10f
Fig. 10g

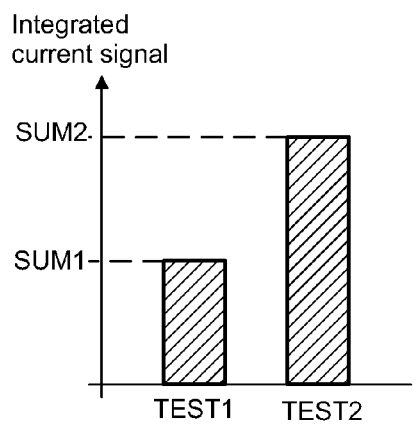
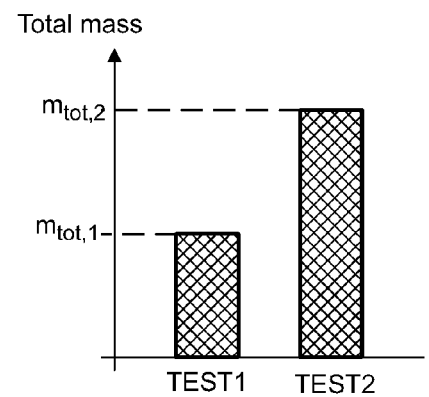
Fig. 12a                    Fig. 12b
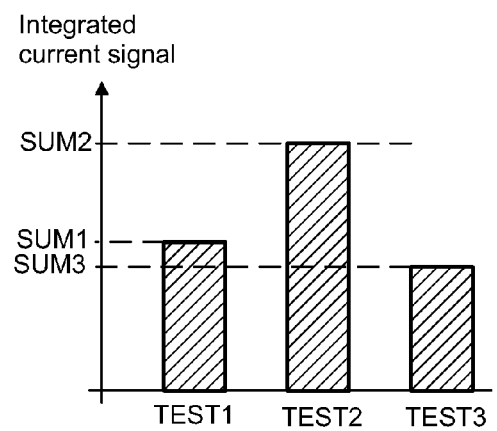
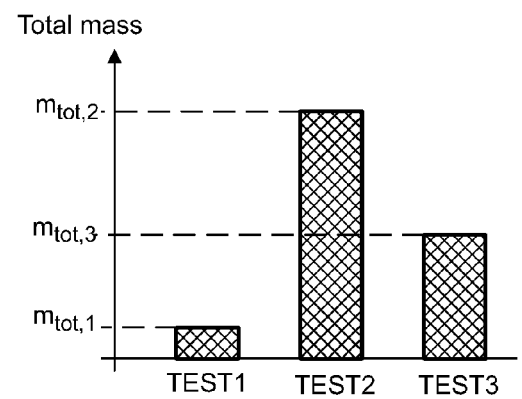
Fig. 13a                    Fig. 13b

METHOD AND APPARATUS FOR MEASURING AEROSOL PARTICLES OF EXHAUST GAS

FIELD

The aspects of the disclosed embodiments relate to measuring aerosol particles.

BACKGROUND

Aerosol measurements may be used e.g. for checking whether the mass concentration of aerosol particles in the exhaust gas of an internal combustion engine is lower than a predetermined limit. The mass concentration of aerosol particles may be measured e.g. by collecting the aerosol particles by a filter, and by weighing the filter in order to determine the total mass of the collected particles. After weighing, the average particle mass concentration may be calculated by dividing the total mass of the collected particles by the total volume of the gas guided through the filter. Collecting a sufficient amount of aerosol particles by the filter may require a relatively long time period, e.g. several hours. Weighing the filter may require manual work, or may require the use of expensive automatic weighing equipment.

SUMMARY

Some versions may relate to an apparatus for measuring aerosol particles. Some versions may relate to a method for measuring aerosol particles.

According to an aspect, there is provided a particle measuring apparatus, comprising:
- a distributor unit arranged to provide a first partial flow and a second partial flow by separating the second partial flow from an input flow,
- a particle collecting unit to collect particles from the first partial flow by using a first filter, and
- a particle monitoring unit to form charged particles by charging particles carried by the second partial flow, and to provide an electric current by collecting the charged particles.

According to an aspect, there is provided a method for measuring aerosol particles, the method comprising:
- providing a first partial flow and a second partial flow by separating the second partial flow from an input flow by using a distributor unit,
- collecting particles from the first partial flow by using a first filter,
- forming charged particles by charging particles carried by the second partial flow, and
- providing an electric current by collecting the charged particles.

The electric current provided by the apparatus may be indicative of the instantaneous concentration of aerosol particles of the input flow. In particular, the electric current may be indicative of the instantaneous active surface area concentration of aerosol particles of the input flow. Thus, the apparatus may be used for measuring the average mass concentration of particles of the input flow, and the apparatus may also provide the electric current, which allows continuous monitoring of the concentration.

A primary electric current generated by collecting the charged particles may be very weak. The apparatus may comprise e.g. an electrometer for measuring the magnitude of the primary electric current, and the apparatus may provide a secondary current signal, which is indicative of the magnitude of the primary electric current. The secondary current signal may be e.g. a digital signal. The secondary current signal may be called e.g. as the monitoring signal. The monitoring signal may be substantially proportional to the primary electric current signal.

The apparatus may be used for detecting rapid changes of the aerosol concentration. The response time of the monitoring signal may be e.g. shorter than 1 s, or even shorter than 0.1 s.

The monitoring signal may be recorded in a memory such that the recorded monitoring signal is associated with time information. The recorded monitoring signal may be associated with one or more time stamps.

The collecting unit of the apparatus may be used for measuring the accumulated mass of particulate matter emitted during a certain collecting time period. Aerosol particles may be captured on the filter of the collecting unit during the particle collecting period. The total mass of particles collected by the filter may be determined by a gravimetric method, and the average mass concentration of the particles may be determined by dividing the total mass with the total volume of gas guided through the filter during the particle collecting period. In particular, the total mass of particles collected by the filter may be determined by weighing the filter after the collecting time period.

The monitoring signal may be recorded such that the recorded monitoring signal may be associated with one or more measurement results determined from the particle sample captured on the filter. In particular, the recorded monitoring signal may be associated with the gravimetrically measured total mass of particles collected on the filter. The recorded monitoring signal may be associated with the average concentration determined from the total mass.

The reliability of a gravimetric measurement result may be improved by using the monitoring signal. A gravimetric measurement result may be classified as valid or invalid by using the monitoring signal. An output result may be determined from one or more valid measurement results such that invalid measurement results do not contribute to the output result.

Analysis of the monitoring signal may allow estimating the validity and/or diagnostic value of one or more measurement results determined from the collected particle sample. A measurement result obtained by weighing the filter may deviate from the true value e.g. due to erroneous handling of the filter. The monitoring signal may be used e.g. for checking the reliability of the gravimetric measurement result. Gravimetric measurement results obtained after several measurement periods may be compared with the monitoring signal in order to determine whether variations of the gravimetric measurement results are correlated with variations of the monitoring signal.

For example, an experiment involving aerosol measurements may be interrupted if analysis of the monitoring signal indicates an abnormal behavior. For example, the experiment may be interrupted if the monitoring signal indicates a change of signal in a situation where a substantially constant value is expected. For example, the experiment may be interrupted if the monitoring signal indicates a constant signal in a situation where a change of the signal is expected. Time spent on failed experiments may be reduced. Evaluating the progress of an experiment based on the monitoring signal may save time and costs.

BRIEF DESCRIPTION OF THE DRAWINGS

In the following examples, several versions will be described in more detail with reference to the appended drawings, in which FIG. 10f shows, by way of example, a side view of the particle monitoring device shown in FIG. 10c, FIG. 10g shows, by way of example, a cover for the particle monitoring device shown in FIG. 10c, FIG. 12a shows, by way of example, an integral of the current signal over a first time period, and an integral of the current signal over a second time period, FIG. 12b shows, by way of example, the total mass of particles collected during the first time period, and the total mass of particles collected during the second time period, FIG. 13a shows, by way of example, an integral of the current signal over a first time period, an integral of the current signal over a second time period, and an integral of the current signal over a third time period, FIG. 13b shows, by way of example, the total mass of particles collected during the first time period, the total mass of particles collected during the second time period, the total mass of particles collected during the third time period.

DETAILED DESCRIPTION

Figure 1:
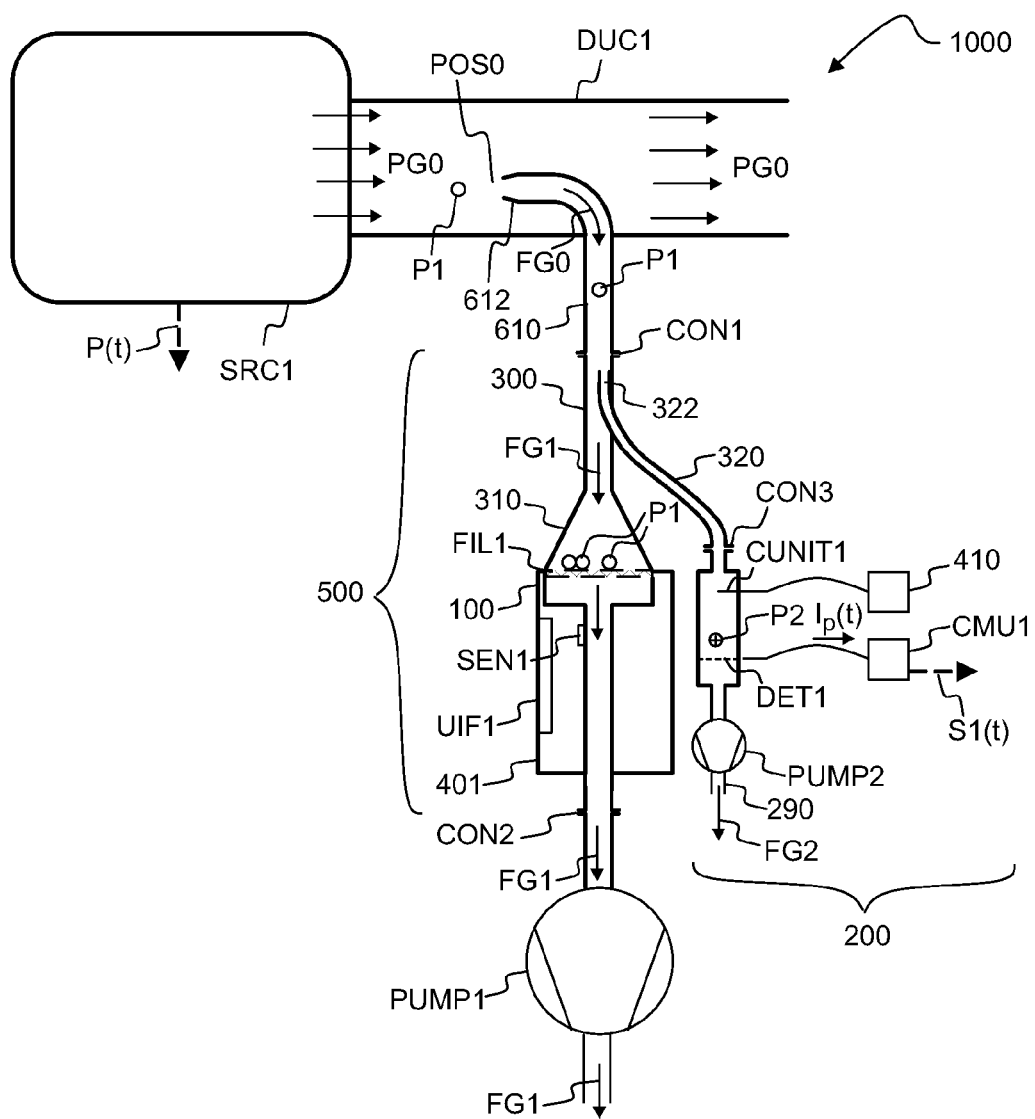
FIG. 1 shows, by way of example, in a cross-sectional view, a particle measuring apparatus connected to operate as a part of an aerosol measurement system.

Referring to FIG. 1, an aerosol measurement system 1000 may be arranged to measure aerosol particles P1 of a primary gas PG0. The primary gas PG0 may carry the aerosol particles P1. The aerosol measurement system 1000 may comprise an aerosol measuring apparatus 500. The aerosol measuring apparatus 500 may collect aerosol particles P1 of the primary gas PG0 to a filter FIL1, and the aerosol measuring apparatus 500 may continuously monitor the concentration of the aerosol particles of the primary gas PG0. The aerosol measuring apparatus 500 may comprise a particle collecting unit 100 for collecting the particles to the filter FIL1, and the aerosol measuring apparatus 500 may comprise a monitoring device 200 for continuous monitoring of the concentration.

The measuring apparatus 500 may be arranged to operate as a part of the aerosol measurement system 1000. The primary gas PG0 may be guided or contained in a gas duct DUC1.

The system 1000 may comprise a sampling nozzle 612 for separating an aerosol sample flow FG0 from the primary gas PG0. The orifice of the sampling nozzle 612 may be located at a sampling point POS0. The aerosol measurement system 1000 may comprise a sampling line 610 to guide an aerosol sample flow FG0 from the gas duct DUC1 to the measuring apparatus 500. The aerosol sample flow FG0 may also be called e.g. as an input flow FG0. The apparatus 500 may comprise a flow distributor unit 300 to divide the input flow FG0 into a first partial flow FG1 and a second partial flow FG2. The flow distributor unit 300 may also be called e.g. as the distributor 300. The first partial flow FG1 may be guided to the filter FIL1, and the second partial flow FG2 may be guided to the monitoring device 200.

Figure 2:
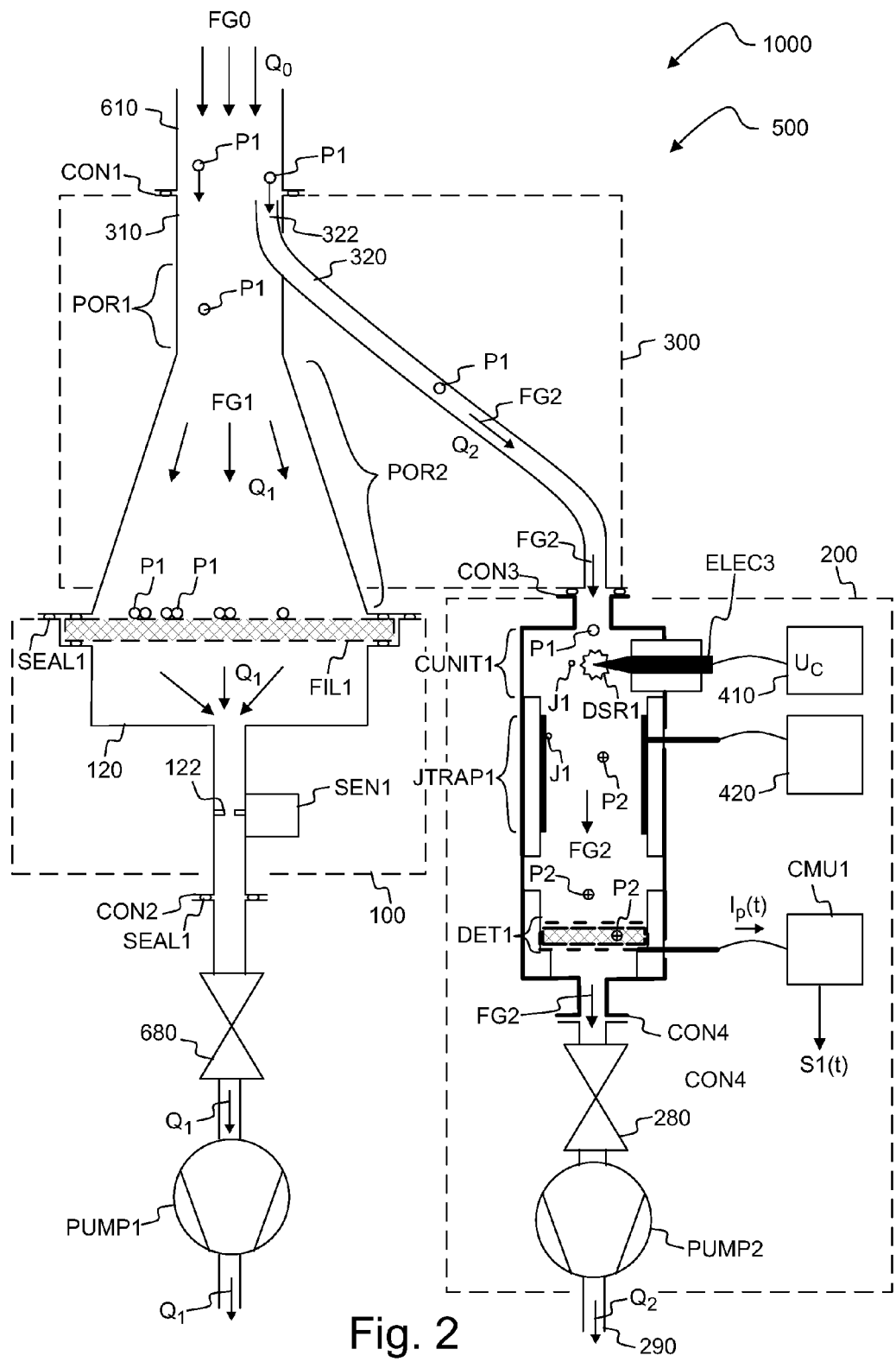
FIG. 2 shows, by way of example, in a cross-sectional view, the particle measuring apparatus.

The monitoring device 200 may comprise a charging unit CUNIT1, which may be arranged to form charged particles P2 by charging particles P1 carried by the second partial flow FG2. The charging unit CUNIT1 may comprise an ion source to generate ions J1. The ions J1 may form charged particles P2 by exchanging charge with neutral particles P1. The ion source may be e.g. a corona discharge DSR1 (FIG. 2). The charging unit CUNIT1 may comprise a corona electrode ELEC3 to generate the corona discharge DSR1.

The monitoring device 200 may comprise a detector DET1 to detect the charge carried by the charged particles P2. The detector DET1 may provide an electric current $I_p(t)$, which may be substantially proportional to the charge of the charged particles captured by the detector DET1 per unit time. The apparatus 500 may comprise a current monitoring unit CMU1 to measure the electric current $I_p(t)$. The current monitoring unit CMU1 may comprise e.g. an electrometer for measuring the magnitude of the electric current $I_p(t)$ conducted from the detector DET1. The current $I_p(t)$ may be conducted from the detector DET1 to the current monitoring unit CMU1. The magnitude of the electric current $I_p(t)$ may be indicative of the instantaneous active surface area concentration of aerosol particles captured by the detector DET1. The electric current $I_p(t)$ may be interpreted to carry a signal, which comprises information about the concentration. The electric current $I_p(t)$ may also be called as the electric current signal $I_p(t)$. The electric current signal $I_p(t)$ may be sent from the detector DET1 to the current monitoring unit CMU1.

The current monitoring unit CMU1 may continuously provide a monitoring signal $S1(t)$ based on the electric current $I_p(t)$ obtained from the detector DET1. The current monitoring unit CMU1 may provide e.g. a digital monitoring signal S1(t) based on the measured electric current $I_p(t)$. The monitoring device 200 may provide a monitoring signal S1(t) which is indicative of the instantaneous concentration of aerosol particles carried by the second partial flow FG2.

The monitoring signal S1(t) may also be indicative of the instantaneous concentration of aerosol particles carried by the sample flow FG0. The monitoring signal S1(t) may also be indicative of the instantaneous concentration of aerosol particles in the primary gas PG0. The concentration of aerosol particles carried by the second partial flow FG2 may be proportional to the concentration of aerosol particles carried by the input flow FG0. The concentration of aerosol particles carried by the second partial flow FG2 may be proportional to the concentration of aerosol particles in the primary gas PG0. The dimensions of the sampling nozzles 612, 322 and the gas flow rates of the flows FG1, FG2 may be selected such that the concentration of aerosol particles P1 carried by the second partial flow FG2 is substantially equal to the concentration of aerosol particles in the primary gas PG0. In particular, the dimensions of the sampling nozzles 612, 322 and the gas flow rates of the flows FG1, FG2 may be selected such that the size distribution of aerosol particles carried by the second partial flow FG2 is substantially equal to the size distribution of aerosol particles in the primary gas PG0.

The aerosol measuring apparatus 1000 may optionally comprise a dilution system for providing a diluted input flow FG0 from a sample flow extracted from the primary gas PG0. The sample flow may be optionally diluted according to a dilution ratio. The dilution ratio may be constant or the dilution ratio may vary e.g. according to the flow rate of the exhaust gas guided to a dilution system. For example, the exhaust gas of an engine may be guided to a tunnel of a Constant Volume Sampler such that the dilution ratio may vary during a particle emission experiment, e.g. according to the output power of the engine.

The flow rate $Q_1$ of the first partial flow FG1 may be controlled by a pump PUMP1 and/or by a valve 680 (FIG. 2). The aerosol measurement system 1000 may comprise a pump PUMP1 to draw the gas flow FG1 through the filter FIL1. The apparatus 500 may be connected to the sample line 610 e.g. by a fluid connector CON1. The apparatus 500 may be (directly or indirectly) connected to the pump PUMP1 e.g. by a fluid connector CON2. The valve 680 may be e.g. a controllable magnetic valve. The pump PUMP1 and/or by a valve 680 may be external components. The apparatus 500 does not need to comprise the pump PUMP1 and/or by a valve 680. An system 1000 may comprise the pump PUMP1 and/or the valve 680 such that the apparatus 500 does not comprise said pump PUMP1 and/or said valve 680.

The apparatus 500 may comprise a second pump PUMP2 to draw the second partial flow FG2 through the monitoring device 200. The second partial flow FG2 may be controlled e.g. based on the flow rate $Q_1$ of the gas flow FG1.

The filter FIL1 of the collecting unit 100 may provide a collected sample of aerosol particles P1. The filter FIL1 may be a replaceable part. The aerosol measuring apparatus 500 may be initially manufactured and provided without the filter FIL1. Particles may be captured to a filter FIL1 during a particle collecting period, and the filter FIL1 may be removed from the collecting unit 100 after the particle collecting period. A new filter may be installed to the collecting unit 100 before each particle collecting period.

After the second partial flow FG2 has been drawn through the pump PUMP2, the second partial flow FG2 may be discharged from an outlet 290 e.g. into the ambient air outside the apparatus 500, or into a ventilation duct.

The apparatus 500 may optionally comprise a valve 280 for controlling the second partial flow FG2. The system 1000 may optionally comprise a valve 680 for controlling the first partial flow FG1.

The apparatus 500 may optionally comprise a sensor SEN1 for monitoring the flow rate of the first partial flow FG1. The apparatus 500 may comprise a sensor SEN1 for measuring the flow rate of the first partial flow FG1.

The apparatus 500 may comprise a voltage supply 410 to provide operating power for the charging unit CUNIT1. The apparatus 500 may comprise a high voltage supply 410 to provide a high voltage to a corona electrode ELEC3 of the charging unit CUNIT1.

The apparatus 500 may optionally comprise a user interface UIF1 for providing information to a user, and/or to receive user input from a user. The apparatus 500 may comprise a frame 401. The frame 401 may mechanically support e.g. the monitoring device 200 and/or the user interface UIF1.

The primary gas PG0 may carry aerosol particles, which may be provided by an aerosol particle source SRC1. The source SRC1 may be e.g. an internal combustion engine. The internal combustion engine may use e.g. natural gas, synthetic gas, gasoline, diesel fuel, fuel oil and/or alcohol as the fuel during a particle emission test. The sample flow FG0 may be taken e.g. before or after gas cleaning unit of the engine. The gas cleaning unit may comprise e.g. a catalytic converter and/or a gas cleaning filter.

The gas duct DUC1 may be e.g. an exhaust gas duct of an engine SRC1. The duct DUC1 may be a duct of a dilution system, wherein gas PG0 may be e.g. diluted exhaust gas of an engine. The duct DUC1 may be e.g. the tunnel of a constant volume sampler (CVT tunnel). The duct DUC1 may comprise diluted exhaust gas. The source SRC1 may also be e.g. a combustion furnace, an incineration furnace, a fluidized bed boiler, an industrial process unit, or a gas turbine. The gas duct DUC1 may be e.g. a flue gas duct of a combustion facility. During a particle collecting period, the apparatus 500 may be optionally kept e.g. in a heated oven e.g. in order to stabilize condensation.

The source SRC1 may optionally provide a process indicator signal P(t). The monitor signal S1(t) may be compared with the process indicator signal P(t) in order to determine whether a change of an operating parameter of the particle source SRC1 corresponds to a change of the monitor signal S1(t). The monitor signal S1(t) may be compared with the process indicator signal P(t) in order to determine whether the monitor signal S1(t) correlates with the process indicator signal P(t). The process indicator signal P(t) may be e.g. indicative of fuel flow rate, input air flow rate to an engine, operating temperature of an engine, operating temperature of a cylinder of an engine, operating temperature of a catalytic converter, operating temperature of a filter, operating temperature of a process, gas pedal setting, valve timing of an engine, fuel feeding pressure, rotation speed of a dynamometer coupled to the engine, torque of an engine, power transferred from an engine to a dynamometer, or flow rate of an additive. The aerosol particle source SRC1 may simultaneously provide a plurality of process indicator signals, which may be indicative of different operating parameters of the source SRC1.

The aerosol measuring apparatus 1000 may optionally comprise a dilution system for diluting the sample flow FG0. The dilution ratio may be determined and/or adjusted based on analysis of the signal S1(t) obtained from the monitoring unit 200. The dilution ratio may be controlled based on the current signal $I_p(t)$. For example, the dilution ratio may be set according to a determined value before the start of a particle collecting period.

Referring to FIG. 2, the input gas flow FG0 may carry aerosol particles P1. The particles P1 may be e.g. solid or liquid particles. The size of the aerosol particles P1 may be e.g. in the range of 5 nm to 50 μm. The input gas flow FG0 containing the particles P1 may also be called as the input aerosol flow FG0.

The distributor 300 may provide the first partial flow FG1 and the second partial flow FG2 by sampling the second partial flow FG2 from the input gas flow FG0. The gas flows FG0, FG1, FG2 may carry aerosol particles P1. The first partial flow FG1 may be guided to the particle collecting unit 100. The second partial flow FG2 may be guided to the monitoring device 200. The detector DET1 of the monitoring device 200 may provide an electric current $I_p(t)$, which is indicative of the concentration of the aerosol particles P1 carried by the input gas flow FG0. The apparatus 500 may provide an electric current $I_p(t)$, which is indicative of the concentration of the aerosol particles P1 carried by the second partial flow FG2. The apparatus 500 may provide a monitoring signal S1(*t*), which is indicative of the concentration of the aerosol particles P1 carried by the second partial flow FG2.

The distributor 300 may comprise a secondary sampling nozzle 322 for separating the second partial flow FG2 from the input gas flow FG0. The second partial flow FG2 may be guided to the monitoring device 200 by a secondary duct 320. The nozzle 322 may also provide the first partial flow FG1 by separating the second partial flow FG2 from the input gas flow FG0. The apparatus 500 may comprise a primary duct 310 for guiding the first partial flow FG1 to the filter FIL1. The dimensions and the geometry of the nozzle 322 may be selected such that the particle size distribution of the first partial flow FG1 is substantially equal to the particle size distribution of the input flow FG0. The primary flow FG0 may have a flow rate $Q_0$. The first partial flow FG1 may have a flow rate $Q_1$. The second partial flow FG2 may have a flow rate $Q_2$. The flow rate $Q_0$ may be equal to the sum $Q_1+Q_2$.

The apparatus 500 may comprise a pump PUMP2 for drawing the gas flow FG2 through the monitoring device 200. When the aerosol particles are collected by the filter FIL1, the pump PUMP2 may be arranged to operate such that the flow rate $Q_2$ e.g. is in the range of 0.1% to 10% of the flow rate $Q_1$. The pump PUMP2 may be arranged to operate such that the flow rate $Q_2$ is in the range of 1% to 5% of the flow rate $Q_1$. The pump PUMP2 may be arranged to operate such that the flow rate $Q_2$ is in the range of 1% to 2% of the flow rate $Q_1$.

The apparatus 500 may be connected to operate as a part of an aerosol measurement system 1000. The aerosol measurement system 1000 may comprise e.g. the sample line 610, a valve 680, and a pump PUMP1. The pump PUMP1 may be arranged to draw the first partial flow FG1 through the filter FIL1. The apparatus 500 may be connected between the sample line 610 and the pump PUMP1 e.g. by using connectors CON1, CON2.

The apparatus 500 may comprise e.g. the primary duct 310 and a secondary duct 320. The primary duct 310 may comprise e.g. a straight portion POR1 and a conically diverging portion POR2. The first partial flow FG1 may be guided through the straight portion POR1 and through the diverging portion POR2. The distributor 300 may comprise a secondary sampling nozzle 322. The second partial flow FG2 may be guided through the secondary sampling nozzle 322 and through the secondary duct 320 to the monitoring device 200. The distributor 300 may further comprise at least a portion of the primary duct 310, and at least a portion of the secondary duct 320. The distributor 300 may comprise the ducts 310, 320 and the nozzle 322.

The particle measuring apparatus 500 may be connected to receive the primary flow FG0 from a sample line 610. The particle measuring apparatus 500 may be connected to a pump PUMP1 so as to draw the flow FG1 through the collecting unit 100 of the apparatus 500. The collecting unit 100, the monitoring device 200, and the distributor 300 may be attached to each other such that the apparatus 500 may be handled manually as a single entity.

The apparatus 500 may be connected between the sample line 610 and the pump PUMP1 e.g. by using connectors CON1, CON2. The apparatus 500 may comprise a fluid connector CON1 for connecting the distributor 300 to the sample line 610 of an aerosol measurement system 1000. The apparatus 500 may be separated from the sample line 610 by opening the connector CON1. The apparatus 500 may be separated from the pump PUMP1 by opening the connector CON2. The connector CON1 and/or CON2 may be e.g. a threaded connector, a flange connector or a quick release connector. For example, the distributor 300 may comprise a threaded portion, which may be arranged to operate as the connector CON1. For example, the distributor 300 may comprise a sealed flange, which may be arranged to operate as the connector CON1. For example, the distributor 300 may comprise a quick release fitting CON1. If needed, the connectors CON1, CON2 may be optionally sealed by seals SEAL1.

The distributor 300 may be removably attached to the collecting unit 100 e.g. so as to allow easy replacement of the filter FIL1.

The monitoring device 200 may be removably attached to the collecting unit 100, to the distributor 300 and/or to the frame 401 e.g. so as to allow easy replacement of the monitoring device 200. The operating life of the monitoring device 200 may be limited e.g. due to contamination, due to particles captured by the detector DET1 and/or due to erosion of the corona electrode ELEC3.

The primary flow FG1 may be guided from the distributor 300 to the filter FIL1 via the primary duct 310. The secondary flow FG2 may be guided from the distributor 300 to the monitoring device 200 via the secondary duct 320. The secondary duct 320 may be implemented e.g. by using a flexible hose or by using metal tubing. The duct 310 and/or 320 may also be a channel formed in a solid piece. The ducts 310, 320 and the secondary nozzle may be formed e.g. by molding or 3D printing.

The secondary duct 320 may be connected to the monitoring device 200 e.g. by a fluid connector CON3. The connector CON3 may be sealed by a seal SEAL1. The secondary duct 320 may also be permanently attached to the monitoring device 200.

The monitoring device 200 may have a limited lifetime. The monitoring device 200 may be a replaceable part of the apparatus 500. The monitoring device 200 may be connected to the distributor 300 e.g. by a fluid connector CON3.

The monitoring device 200 may be connected to the pump PUMP2 e.g. by a fluid connector CON4.

The apparatus 500 may comprise a filter holder 120 for holding a filter FIL1. The collecting unit 100 may comprise the filter holder 120 for holding the filter FIL1.

The filter FIL1 may be optionally supported by one or more supporting elements. The one or more support elements may e.g. prevent bending of the filter FIL1 due to a pressure difference caused by the gas flow FG1. The filter FIL1 may be optionally supported by one or more filter cassette elements.

The apparatus 500 may comprise one or more sealing elements SEAL1 for forming a substantially leak-proof joint between the primary duct 310 and the filter holder 120.

The collecting unit 100 may be arranged to collect particles P1 carried by the first partial flow FG1 to the filter FIL1. The total mass of the collected particles may be determined by a gravimetric method after the particles have been collected. The total mass of the collected particles may be determined e.g. by weighing the filter FIL1 before a measurement period and after the measurement period, and by determining the change of weight. In case of combustible particles, the total mass of the collected particles may be determined also by combusting the particles, and by measuring the resulting change of weight. The filter FIL1 may be weighed with or without the optional support elements.

Weighing the filter FIL1 may provide a gravimetric measurement result about the total weight of the collected particles. The collecting unit 100 may be arranged to operate such that more than 99% of the first partial flow FG1 is guided through the filter FIL1. The collecting unit 100 may be arranged to operate such that more than 99.9% of the first partial flow FG1 is guided through the filter FIL1. The filter FIL1 may comprise e.g. a fibers and or porous material to collect aerosol particles. The material of the filter FIL1 may be e.g. polycarbonate, polystyrene, glass, or sintered metal. The filter FIL1 may be selected such that e.g. more than 99.5% of particles having an aerodynamic diameter of 0.3 µm may be collected by the filter FIL1. The filter FIL1 may collect aerosol particles e.g. by interception, inertial impaction, diffusion, gravitational settling and/or electrostatic collection.

The apparatus 500 may comprise a flow sensor SEN1 for monitoring the flow rate of the first partial flow FG1. The apparatus 500 may optionally comprise a constriction 122 to cause a pressure difference, which depends on the flow rate $Q_1$ of the first partial flow FG1. The operation of the flow sensor may be based on e.g. monitoring pressure difference or a change of temperature caused by the flow. The flow sensor SEN1 may be e.g. a pressure sensor, which measures the pressure downstream the filter FIL1. The flow sensor SEN1 may be e.g. a pressure difference sensor, which measures the pressure difference over the constriction 122. The flow sensor SEN1 may be e.g. a thermal mass flow sensor. The flow sensor SEN1 may be arranged to measure the flow rate $Q_1$ of the first partial flow FG1, or the flow sensor SEN1 may be arranged to detect when the flow rate $Q_1$ is above or below a predetermined limit.

Figure 3:
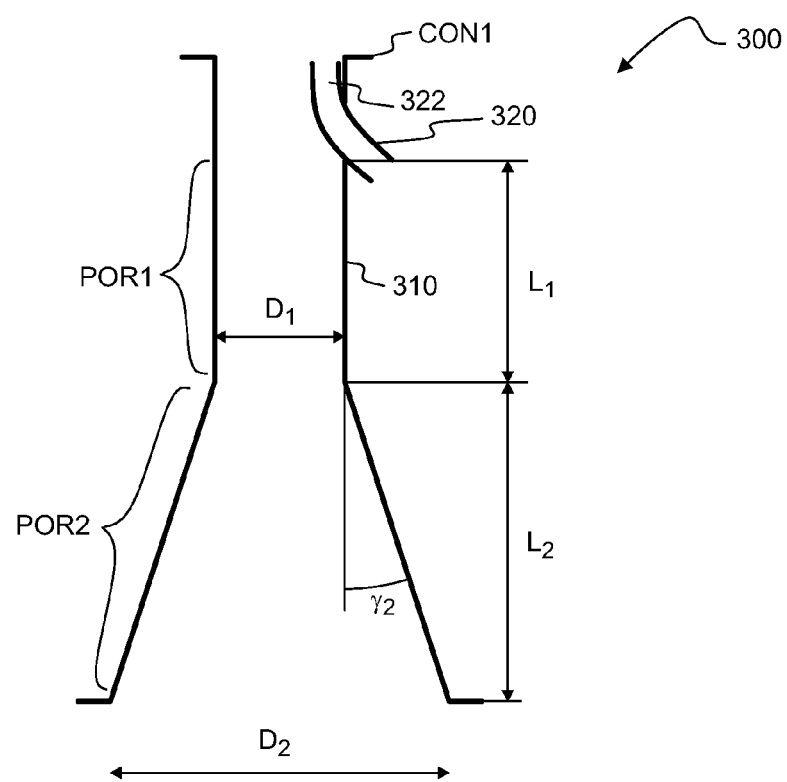
FIG. 3 shows, by way of example, in a cross-sectional side view, the dimensions of a primary duct of the measuring apparatus.

Referring to FIG. 3, the primary duct 310 of the apparatus 500 may comprise a substantially straight portion POR1, and a conically diverging portion POR1. The portions POR1, POR2 may be e.g. axially symmetric. The distributor 300 may comprise the portions POR1, POR2. The straight portion POR1 may have an inner diameter $D_1$. The conically diverging portion POR1 may have an inner diameter $D_2$ at the outlet end of the primary duct 310. The straight portion POR1 may have a length $L_1$. The conically diverging portion POR1 may have a length $L_2$. The conically diverging portion POR1 may have a half cone angle $\gamma_2$.

The internal dimensions of the primary duct 310 may comply e.g. with dimensions defined in a technical standard or official regulation for exhaust gas emission measurement. In particular, the internal dimensions of the primary duct 310 may comply e.g. with the dimensions defined in CFR 40 part 40 subpart N, pages 161-162, as in force on 17 Aug. 2015. CFR means the Code of Federal Regulations of the United States of America.

The diameter $D_1$ may be e.g. substantially equal to 9 mm.

The diameter $D_2$ may be e.g. substantially equal to 39 mm.

The length $L_1$ may be e.g. greater than or equal to 24 mm,

The length $L_2$ may be e.g. substantially equal to 67 mm.

The half cone angle $\gamma_2$ may be e.g. substantially equal to 12.5°.

The inner surfaces of the primary duct 310 may be made of electrically conductive material e.g. in order to minimize electrostatic collecting of particles to the inner wall of the primary duct 310. In particular, the inner surfaces of the primary duct 310 may be made of a metal (e.g. stainless steel).

The primary duct 310 may also be implemented by using two or more parts, which may be removably attached to each other. For example, a distributor 300 and an extension unit 330 may together form the primary duct 310 (FIG. 9b).

Figure 4A:
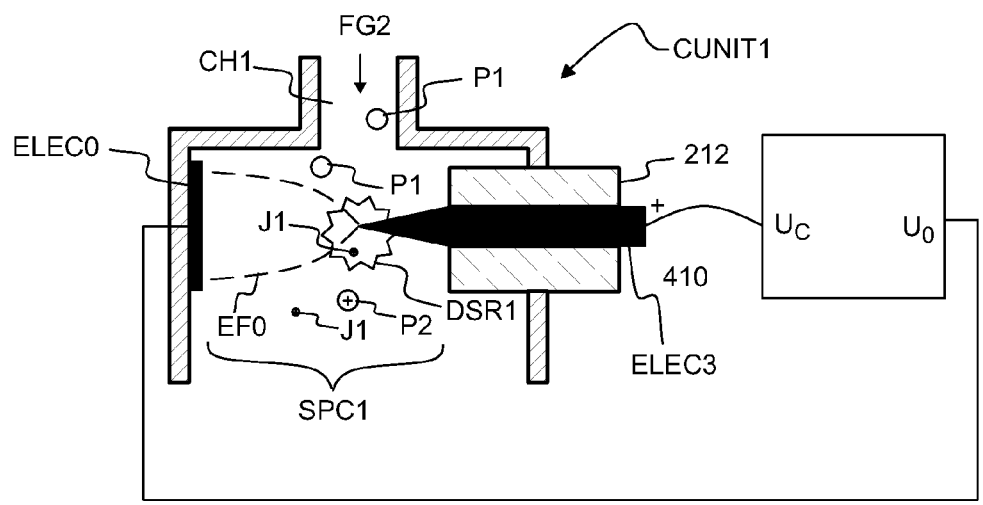
FIG. 4a shows, by way of example, in a cross-sectional view, a charging unit of the particle monitoring device of the particle measuring apparatus
Figure 4B:
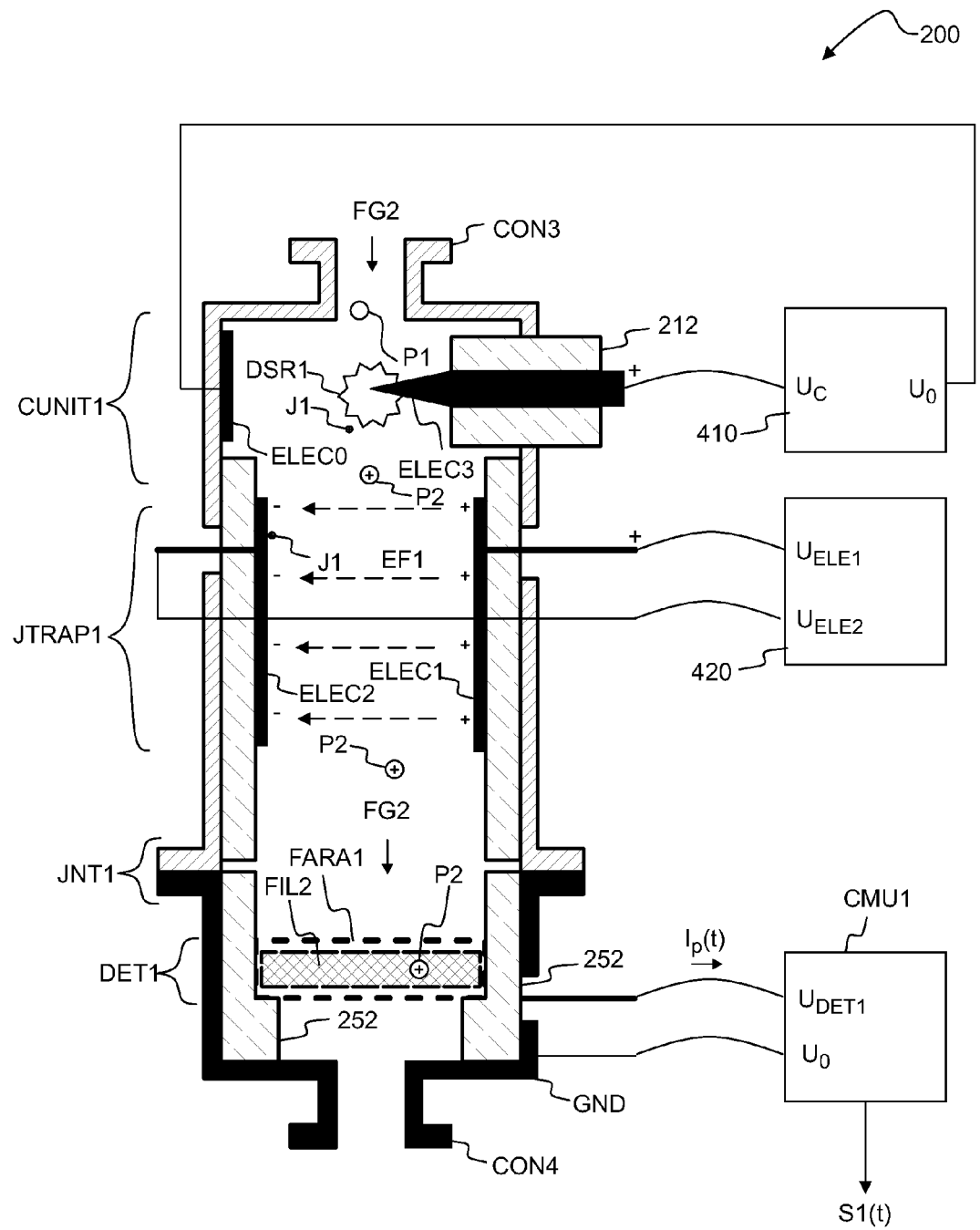
FIG. 4b shows, by way of example, in a cross-sectional view, the particle monitoring device.

Referring to FIGS. 4a and 4b, the monitoring device 200 may comprise a charging unit CUNIT1 and a charge detector DET1. The charging unit CUNIT1 may provide charged particles P2 by charging at least a part of the particles P1 carried by the second partial flow FG2. The charging unit CUNIT1 may convert at least a part of the particles P1 of the flow FG2 into charged particles P2. The charging unit CUNIT1 may comprise a corona electrode ELEC3 for generating ions J1. The ions J1 may form charged particles P2 by exchanging charge with neutral particles P1. The charging of the particles may take place in a charging space SPC1 of the charging unit CUNIT1. The detector DET1 may be arranged to detect the charge of the charged particles P2.

The corona electrode ELEC3 may be arranged to produce ions J1 by corona discharge DSR1. The corona electrode ELEC3 may operate together with a counter-electrode ELEC0. The electrodes ELEC3, ELEC0 may be connected to the high voltage supply 410 such that the electrodes ELEC3, ELEC0 have a voltage difference $U_C-U_0$. The corona electrode ELEC3 and the counter-electrode ELEC0 may together form an electric field EF0, which generates the corona discharge DSR1. The strength of the electric field EF0 may locally exceed the dielectric strength of the gas guided through the charging space between the electrodes ELEC0, ELEC3 so that the corona discharge DSR1 may be formed in the vicinity of the corona electrode ELEC3.

The corona electrode ELEC3 may be e.g. a conductor which has a sharp tip. The corona electrode may be e.g. an exposed conductor wire which has a narrow diameter. The corona electrode may be electrically insulated by one or more insulators 212. The corona electrode may be mechanically supported by one or more insulators 212. The corona electrode may be connected to a high voltage supply 410. The corona electrode may have a high voltage $U_C$. The device 200 may comprise a high voltage supply 410 to provide a high voltage $U_C$ to the corona electrode. The counter-electrode ELEC0 may have e.g. a voltage $U_0$.

The charge detector DET1 may provide an electric current $I_p(t)$, which is proportional to the charge of the charged particles captured by the detector DET1 per unit time. The detector DET1 may collect the charged particles P2 of the flow FG2. The detector DET1 may comprise e.g. a particle filter DFIL for capturing the charged particles P2. The filter DFIL may be called e.g. as a monitoring filter. The filter DFIL may be electrically conductive or electrically insulating. The filter DFIL may be surrounded by a Faraday cage FARA1, or an electrically conductive outer layer of the filter DFIL may operate as the Faraday cage FARA1. An electrically conductive filter DFIL may comprise e.g. sintered conductive particles or conductive fibers. The Faraday cage FARA1 and/or the conductive filter DFIL may be galvanically connected to the current monitoring unit CMU1. The charge carried by charged particles P2 may be detected by using the Faraday cage FARA1 and the current monitoring unit CMU1 also in a situation where the charged particles P2 captured by the filter DFIL inside the Faraday cage FARA1 do not touch the Faraday cage FARA1.

The instantaneous magnitude of the electric current $I_p(t)$ may be measured by the current monitoring unit CMU1. The current monitoring unit CMU1 may provide a monitor signal $S1(t)$, which is indicative of the electric current $I_p(t)$. The current monitoring unit CMU1 may provide a monitoring signal $S1(t)$ from the electric current $I_p(t)$. The monitoring signal $S1(t)$ may be substantially proportional to the electric current $I_p(t)$. The monitoring signal $S1(t)$ may be e.g. a digital signal or an analog signal. The monitoring signal $S1(t)$ may be indicative of the instantaneous concentration of particles P1 guided to the monitoring device 200. The current monitoring unit CMU1 may comprise e.g. an electrometer for measuring the current $I_p(t)$. The current monitoring unit CMU1 may be arranged to measure the electric current $I_p(t)$ conducted from the detector DET1 to an electrical ground GND of the monitoring device 200. The detector DET1 may be electrically insulated from an electrical ground GND of the monitoring device 200 such that the current monitoring unit CMU1 may measure the electric current $I_p(t)$ conducted from the detector DET1 to the electrical ground GND via the current monitoring unit CMU1. The detector DET1 may be supported e.g. by one or more insulators 252.

The electrical ground GND may have a voltage $U_0$. The current monitoring unit CMU1 may be arranged to keep the voltage $U_{DET1}$ of the detector DET1 close to the voltage $U_0$ of the electrical ground GND. The voltage $U_{DET1}$ of the detector DET1 may be kept close to the voltage $U_0$ of the electrical ground GND during monitoring the electric current $I_p(t)$. The absolute value of the difference ($U_{DET1}-U_0$) between the voltage $U_{DET1}$ of the detector DET1 and the voltage $U_0$ of the electrical ground may be e.g. smaller than 10 V.

The filter DFIL may collect particles irreversibly such that the particles are not released from the detector DET1 back into the gas flow. The detector DET1 may collect particles during the measurement period such that e.g. less than 10% of the mass of the collected particles is released from the detector DET1 back into to gas flow during the measurement period. Particles collected by the detector DET1 may eventually contaminate and/or block the detector DET1. If needed, the detector DET1 may be cleaned or replaced with a clean detector. The monitoring device 200 may optionally comprise one or more joints JNT1, which may be opened in order to replace the detector DET1.

The monitoring unit 200 may optionally comprise an ion trap JTRAP1 to remove ions J1 from the flow FG2. The ion trap JTRAP1 may be positioned downstream of the charging unit CUNIT1 and upstream of the detector DET1. The ion trap JTRAP1 may remove at least a part of the ions J1 from the second partial flow FG2, which is guided to the detector DET1. Using the ion trap JTRAP1 may stabilize the electric current $I_p(t)$. The ion trap JTRAP1 may comprise e.g. two or more electrodes ELEC1, ELEC2 to provide an electric field EF1, which may deflect ions J1 away from the flow FG2. The electric field EF1 may be substantially transverse with respect to the direction of the gas flow FG2 passing through the electrodes ELEC1, ELEC2. The ion trap JTRAP1 may comprise a first electrode ELEC1 and a second electrode ELEC2. The ion trap may comprise e.g. a pair of substantially parallel electrodes ELEC1, ELEC2. The first electrode ELEC1 may have a first voltage $U_1$, and the second electrode ELEC2 may have a second different voltage $U_2$. The electrodes ELEC1, ELEC2 may be coupled to a voltage difference $U_1-U_2$ in order to generate the electric field EF1. The magnitude of the electric field EF1 and/or the velocity of the gas flow may passing through the space the electrodes ELEC1, ELEC2 be selected such that a (first) suitable fraction of the charged particles P2 may pass through the ion trap JTRAP1 and such that a (second) suitable fraction of the ions J1 may be deflected away from the flow FG2. Thus, a large part of the charged particles P2 may pass through the ion trap JTRAP1 to the detector DET1. The lower cut-off size of particles which may pass through the ion trap may be selected by selecting the voltage difference $U_1-U_2$. The voltage $U_1$ and/or the voltage $U_2$ may be generated by a voltage supply 420.

The apparatus 500 may comprise the pump PUMP2 for drawing the secondary gas flow FG2 through the monitor device 200. The pump PUMP2 may be e.g. a diaphragm pump, a piston pump, a rotary vane pump, or a peristaltic pump. The secondary gas flow FG2 guided through the monitor device 200 may be vented e.g. into the atmosphere or into a ventilation duct.

The pump PUMP2 may be positioned downstream of the detector DET1 so that the pump PUMP2 does not remove particles from the secondary gas flow FG2 before the particles P2 are detected by the detector DET1.

The apparatus 500 may optionally comprise a valve 280 for controlling the flow rate $Q_2$ of the secondary gas flow FG2. The valve 280 may be e.g. a controllable magnetic valve. The valve 280 may be positioned downstream of the detector DET1.

The apparatus 500 may be arranged to operate such that the flow rate through the first pump PUMP1 is equal to the flow rate through the filter FIL1.

The flow rate $Q_1$ of the primary gas flow FG1 may be regulated by one or more components, which are positioned downstream the filter FIL1. The secondary gas flow FG2 may be drawn through the detector DET1 such that the secondary gas flow FG2 is not combined with the primary gas flow FG1 downstream of the filter FIL1. Keeping the secondary gas flow FG2 separate from the primary gas flow FG1 may help to ensure that the secondary gas flow FG2 does not cause an error to the flow rate $Q_1$ drawn through the filter FIL1.

Figure 5:
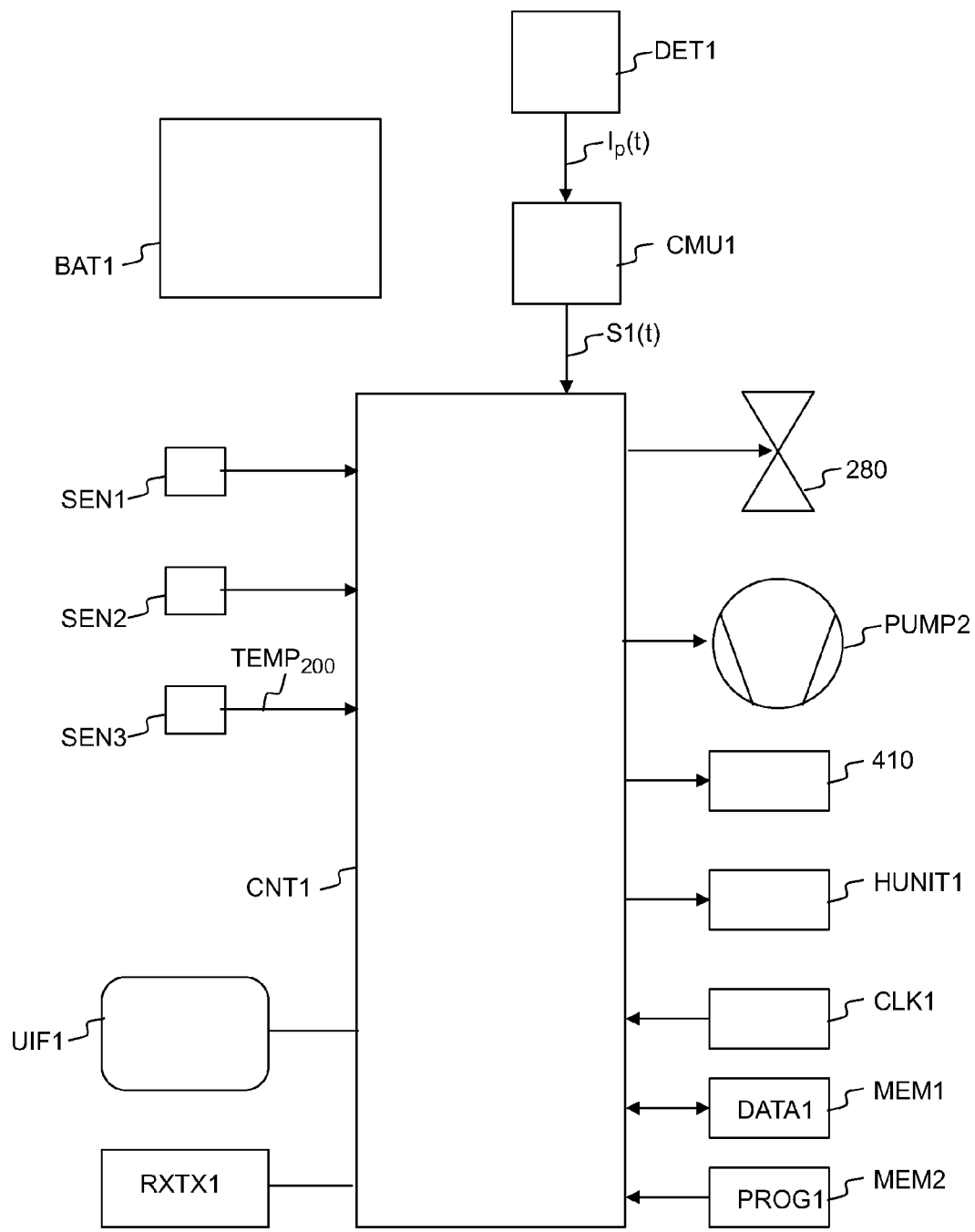
FIG. 5 shows, by way of example, a control system of the particle measuring apparatus.

FIG. 5 shows, by way of example, a control system of the particle measuring apparatus 500. The apparatus 500 may comprise a control unit CNT1 for processing measured data and/or for controlling operation of the apparatus 500. The apparatus 500 may comprise the pump PUMP2 to draw the secondary flow FG2 through the monitor device 200. The apparatus 500 may optionally comprise a valve 280 to control the secondary flow FG2.

The apparatus 500 may comprise the detector DET1 for providing the electric current signal $I_p(t)$. The apparatus 500 may comprise the current monitoring unit CMU1 to provide the monitor signal $S1(t)$ from the current signal $I_p(t)$. The apparatus 500 may comprise a memory MEM1 for storing measured data DATA1. The data DATA1 may comprise e.g. the measured signal $I_p(t)$ and/or $S1(t)$.

The apparatus 500 may comprise a memory MEM2 for storing computer program PROG1. The computer program PROG1 may comprise computer program code configured to, when executed on at least one data processor, cause the control unit CNT1 to control operation of the apparatus 500. The computer program PROG1 may comprise computer program code configured to, when executed on at least one data processor, cause processing of measured data (e.g. the signals $I_p(t)$, $S1(t)$). The computer program PROG1 may comprise computer program code configured to, when executed on at least one processor, cause the apparatus 500 to provide a control signal for starting and/or stopping the first partial flow FG1 based on the monitoring signal $S1(t)$.

The apparatus 500 may optionally comprise a communication unit RXTX1 for receiving and/or transmitting data. The communication unit RXTX1 may transmit e.g. the monitoring signal $S1(t)$ e.g. to an external portable computer. The communication unit RXTX1 may transmit e.g. the monitoring signal $S1(t)$ e.g. to a control unit of the system 1000. The communication unit RXTX1 may transmit e.g. the monitoring signal $S1(t)$ e.g. to an Internet server. The communication unit RXTX1 may receive and/or transmit data e.g. by using wireless transmission, by using an optical cable and/or by using an electric cable. A command for starting and/or a command for stopping a measurement may be communicated via the communication unit RXTX1 to the control unit CNT1. The computer program PROG1 may be updated by receiving data via the communication unit RXTX1. The computer program PROG1 may be updated by receiving data e.g. from an Internet server.

The apparatus 500 may optionally comprise a clock CLK1 to provide time information. The monitoring signal $S1(t)$ may be recorded in the memory MEM1 as data DATA1 such that the recorded monitoring signal $S1(t)$ is associated with the time information. The monitoring signal $S1(t)$ may be recorded in the memory MEM1 as a function $S1(t)$ of time t. The data DATA1 may be time-stamped.

The apparatus 500 may optionally comprise a user interface UIF1 for providing information to a user and/or for receiving user input from a user. The user interface UIF1 may comprise e.g. a display and one or more keys. The user interface UIF1 may comprise e.g. a touch screen. The user interface UIF1 may be arranged to display e.g. the magnitude of the electric current $I_p(t)$. The interface UIF1 may be arranged to provide visual indication of the magnitude of the electric current ($I_p(t)$). The interface UIF1 may be arranged to display e.g. a curve, which indicates the magnitude of the electric current ($I_p(t)$).

The units 100, 200, 300 may be positioned e.g. in a heated cabinet, close to a running engine and/or close to a dilution system. The interface UIF1 may also be remote from the units 100, 200, 300 e.g. so that the interface UIF1 may be located at an ergonomic and/or safe position. A portable computer or a mobile device (e.g. a smartphone) may be arranged to communicate with the apparatus 500 via the communication unit RXTX1, and said portable computer or mobile device may be arranged to operate as the interface UIF1.

Data measured by the device 200 may also be processed in a distributed manner. For example, temperature compensation, compensation of a background and/or data correlation analysis may be performed in a separate data processor. The data may be processed e.g. by a portable computer and/or by using an internet server.

The apparatus 500 may optionally comprise a rechargeable battery BAT1 e.g. for providing operating power e.g. for one or more of the following parts: the control unit CNT1, the high voltage supply 410, the charge monitoring unit CMU1, and/or the pump PUMP2. Thanks to using the battery, the apparatus 500 does not need to be connected to an electric power line during operation of the apparatus 500. After the particle collecting period, the apparatus 500 may be disconnected from the sample line 610, and moved to a location, which is remote from the sample line 610. The battery may be re-charged at a location, which is remote from the sampling line 610.

The apparatus 500 may comprise a high voltage supply 410 for providing operating voltage $U_C$ to the corona electrode ELEC3. The apparatus 500 may be arranged to control operation of the high voltage supply 410.

The apparatus 500 may optionally comprise one or more heating elements HUNIT1. The heating element HUNIT1 may be arranged to stabilize the operating temperature of the current monitoring unit CMU1. The heating element HUNIT1 may be arranged to keep the operating temperature of the current monitoring unit CMU1 substantially constant.

The apparatus 500 may comprise a flow sensor SEN1 to monitor the flow rate of the first partial flow FG1.

The apparatus 500 may comprise a flow sensor SEN2 to monitor the flow rate of the second partial flow FG2 and/or to monitor the pressure difference of the detector DET1. The flow resistance of the detector DET1 may increase during operation due to particles captured to the filter DFIL. The flow rate $Q_2$ of the second partial flow FG2 may depend on the flow resistance of the detector DET1. The apparatus 500 may comprise a sensor SEN2 for monitoring the pressure difference caused by the detector DET1. The sensor SEN2 may be e.g. a pressure sensor, which measures the pressure downstream the detector DET1. The sensor SEN2 may be e.g. a pressure difference sensor, which measures the pressure difference over the detector DET1. The sensor SEN2 may be e.g. a flow sensor, which may be arranged to monitor the flow rate $Q_2$ of the second partial flow FG2. The operation of the sensor SEN2 may be based on e.g. monitoring pressure difference or a change of temperature caused by the flow FG2.

The apparatus 500 may be arranged to control the pump PUMP2 based on a signal obtained from the sensor SEN2 so as to keep the flow rate $Q_2$ in a predetermined range. For example, the apparatus 500 may be arranged to adjust a rotation speed of a motor of the pump PUMP2 based on a signal obtained from the sensor SEN2.

The apparatus 500 may be arranged to detect when the flow resistance of the detector DET1 exceeds a predetermined limit. The detector DET1 may be replaced or cleaned if the flow resistance of the detector DET1 exceeds the predetermined limit. The apparatus 500 may be arranged to provide an indication to a user when the flow resistance of the detector DET1 exceeds a predetermined limit. The indication may be provided e.g. by using the user interface UIF1.

The apparatus 500 may optionally comprise one more pressure sensors to monitor the pressure difference over the filter FIL1. The pressure difference may depend on the amount of particles collected by the filter FIL1. The pressure difference may be indicative of the amount of particles collected by the filter FIL1. The apparatus 500 may be arranged to record the pressure difference over the filter FIL1 as a function of time. The apparatus 500 may be arranged to provide an indication to a user when the pressure difference over the filter exceeds a predetermined value. The apparatus 500 may be arranged to stop the first partial flow FG1 when the pressure difference over the filter exceeds a predetermined value.

The charging unit CUNIT1 may be arranged to operate such that the corona discharge is switched on only when the flow rate $Q_2$ through the charging space SPC1 is greater than a predetermined limit. The charging unit CUNIT1 may be arranged to operate such that the corona discharge is switched off when the gas flow rate $Q_2$ of the gas flow FG2 smaller than the predetermined limit. The voltage supply 410 may be controlled based on the flow rate $Q_2$ of the flow FG2. When the flow FG2 is controlled based on the flow rate $Q_1$ of the flow FG1, the voltage supply 410 may also be controlled based on the flow rate $Q_1$.

The monitoring signal $S1(t)$ may drift e.g. due to a change of operating temperature of the current monitoring unit CMU1, due to erosion of a corona electrode ELEC3 and/or due to contamination of the flow channels. The apparatus 500 may be arranged to at least partly compensate the effect of temperature, erosion and/or contamination on the monitoring signal $S1(t)$.

The operating temperature of the monitoring device 200 may have an effect on the monitoring signal. In particular, a change of the operating temperature of the current monitoring unit CMU1 may cause a change of the monitoring signal even when the particle flow to the monitoring device 200 remains unchanged.

The apparatus 500 may be arranged to stabilize the operating temperature of the current monitoring unit CMU1.

The apparatus 500 may be arranged to monitor the operating temperature of the monitoring device 200. The apparatus 500 may optionally comprise a temperature sensor SEN3 for monitoring the operating temperature TEMP 200 of the current monitoring unit CMU1.

The apparatus 500 may comprise a heating element HUNIT1 arranged to heat the current monitoring unit CMU1. The apparatus 500 may be arranged to control the heating element HUNIT1 e.g. based on temperature information $TEMP_{200}$ obtained from the temperature sensor SEN3.

The voltage supply 410 may feed electric power to the corona electrode ELEC3. The voltage supply 410 and the corona discharge DSR1 may convert electric power into heat. The current monitoring unit CMU1 may be located close to the voltage supply 410 and/or close to the corona electrode ELEC3. The operation of the voltage supply 410 and the corona discharge DSR1 may have an effect on the operating temperature of the current monitoring unit CMU1. The corona discharge DSR1 may have a first operating state where the corona discharge DSR1 is operating, and a second operating state where the corona discharge DSR1 is not operating. The voltage supply 410 may have a first active operating state where the corona discharge DSR1 is operating, and a second inactive operating state where the corona discharge DSR1 is not operating. The apparatus 500 may comprise a heating element HUNIT1 arranged to heat the current monitoring unit CMU1. The apparatus 500 may be arranged to control the heating element HUNIT1 based on the operating state of the corona discharge. The apparatus 500 may be arranged to control the heating element HUNIT1 based on the operating state of the voltage supply 410. The apparatus 500 may be arranged to control the heating element HUNIT1 so as to keep the electric power consumption of the monitoring device 200 substantially constant when the operating state of the voltage supply 410 is changed. The voltage supply 410 may have a first heating power, the corona discharge DSR1 may have a second heating power, and the heating element HUNIT1 may have a third heating power. The apparatus 500 may be arranged to control the heating element HUNIT1 so as to keep the sum of said heating powers substantially constant when the operating state of the voltage supply 410 is changed.

The apparatus 500 may be arranged to compensate an effect of the operating temperature on the monitoring signal based on temperature information obtained from the temperature sensor SEN3. The apparatus 500 may be arranged to provide a temperature-compensated monitoring signal $S1(t)$. The apparatus 500 may comprise a memory, which comprises predetermined temperature compensation data. The apparatus 500 may be arranged to provide a temperature-compensated monitoring signal $S1(t)$ from the current $I_p(t)$ by using information about the measured operating temperature and by using the temperature compensation data.

In an embodiment, a plurality of identical monitoring devices 200 may be manufactured. The temperature compensation data may be determined separately for each individual monitoring device 200. Each individual monitoring device 200 may be associated with temperature compensation data associated with said monitoring device 200. Temperature compensation data associated with a first monitoring device 200 may be different from temperature compensation data associated with a second monitoring device 200. When a first monitoring device 200 is replaced with a second monitoring device 200, the temperature compensation data associated with the second monitoring device 200 may be stored in the memory of the apparatus 500. The temperature compensation data may be e.g. retrieved from an Internet server based on an identification code of the second monitoring device 200. The second monitoring device 200 may also comprise a memory for storing the pre-determined temperature compensation data associated with the second monitoring device 200. The temperature compensation data also may be inputted to a memory of the apparatus 500 manually by using a user interface UIF1.

The monitoring signal $S1(t)$ provided by the device 200 may be compensated e.g. by using a background signal value $S_{REF}$. The background signal value $S_{REF}$ may be determined experimentally e.g. by measuring the electric current signal $I_p(t)$ of the detector DET1 in a situation where the flow FG2 through the detector DET1 is zero. The flow FG2 may be reduced to zero e.g. by closing the valve 280. The flow rate $Q_2$ of the flow FG2 is greater than zero during normal operation. A compensated monitoring signal $S1(t)$ may be determined from the electric current signal $I_p(t)$ measured during the normal operation by using the background signal value $S_{REF}$. The apparatus 500 may be arranged to determine a compensated monitoring signal $S1(t)$ from the electric current signal $I_p(t)$ measured during the normal operation by using the background signal value $S_{REF}$.

The apparatus 500 may be arranged to measure a first background signal value $S_{REF1}$ by measuring the electric current $I_p(t_{R1})$ at a first time $t_{REF1}$ when that the flow FG2 is substantially equal to zero. The apparatus 500 may be arranged to measure a second reference value $S_{REF2}$ at a second time $t_{REF2}$ when that the flow FG2 is substantially equal to zero. The time $t_{REF1}$ may be e.g. before the start of a particle collecting period $T_{tot}$, and the time $t_{REF2}$ may be after the end of a particle collecting period $T_{tot}$. The background signal value $S_{REF2}$ may also be different from the background signal value $S_{REF1}$.

A compensated monitoring signal $S1(t)$ may be determined from the electric current signal $I_p(t)$ measured during the normal operation by using the background signal values $S_{REF1}$ and $S_{REF2}$.

$\Delta S_{REF}$ denotes the change between the signals $S_{REF1}$, $S_{REF2}$. (i.e. $\Delta S_{REF} = S_{REF2} - S_{REF1}$). The validity of the electric current signal $I_p(t)$ measured during normal operation may be evaluated based on the change $\Delta S_{REF}$. The electric current signal $I_p(t)$ may be determined to be valid if the change $\Delta S_{REF}$ is smaller than a predetermined limit. The electric current signal $I_p(t)$ may be determined to be invalid if the change $\Delta S_{REF}$ exceeds the predetermined limit.

The apparatus 500 may be configured to determine the compensated monitoring signal $S1(t)$ from the measured electric current signal $I_p(t)$ by using one or more background signal values $S_{REF1}$, $S_{REF2}$ and/or by using temperature information.

An external data processing device may be configured to determine the compensated monitoring signal $S1(t)$. In particular, a portable computer may be configured to determine the compensated monitoring signal $S1(t)$ from the measured electric current signal $I_p(t)$ by using one or more background signal values $S_{REF1}$, $S_{REF2}$ and/or by using temperature information.

The compensated monitoring signal $S1(t)$ may be determined substantially in real time or after the end of the particle collecting time period $T_{tot}$. The current monitoring unit CMU1 may provide auxiliary signal data $S_{AUX}(t)$, which may be indicative of the instantaneous magnitude of the electric current $I_p(t)$. The compensated monitoring signal $S1(t)$ may be subsequently determined from the auxiliary signal data $S_{AUX}(t)$ by using information about the background signal values $S_{REF1}$, $S_{REF2}$. The auxiliary signal data $S_{AUX}(t)$ may be optionally recorded in a memory, and the compensated monitoring signal $S1(t)$ may be determined from the auxiliary signal data $S_{AUX}(t)$ after the end of the particle collecting time period $T_{tot}$.

Figure 6:
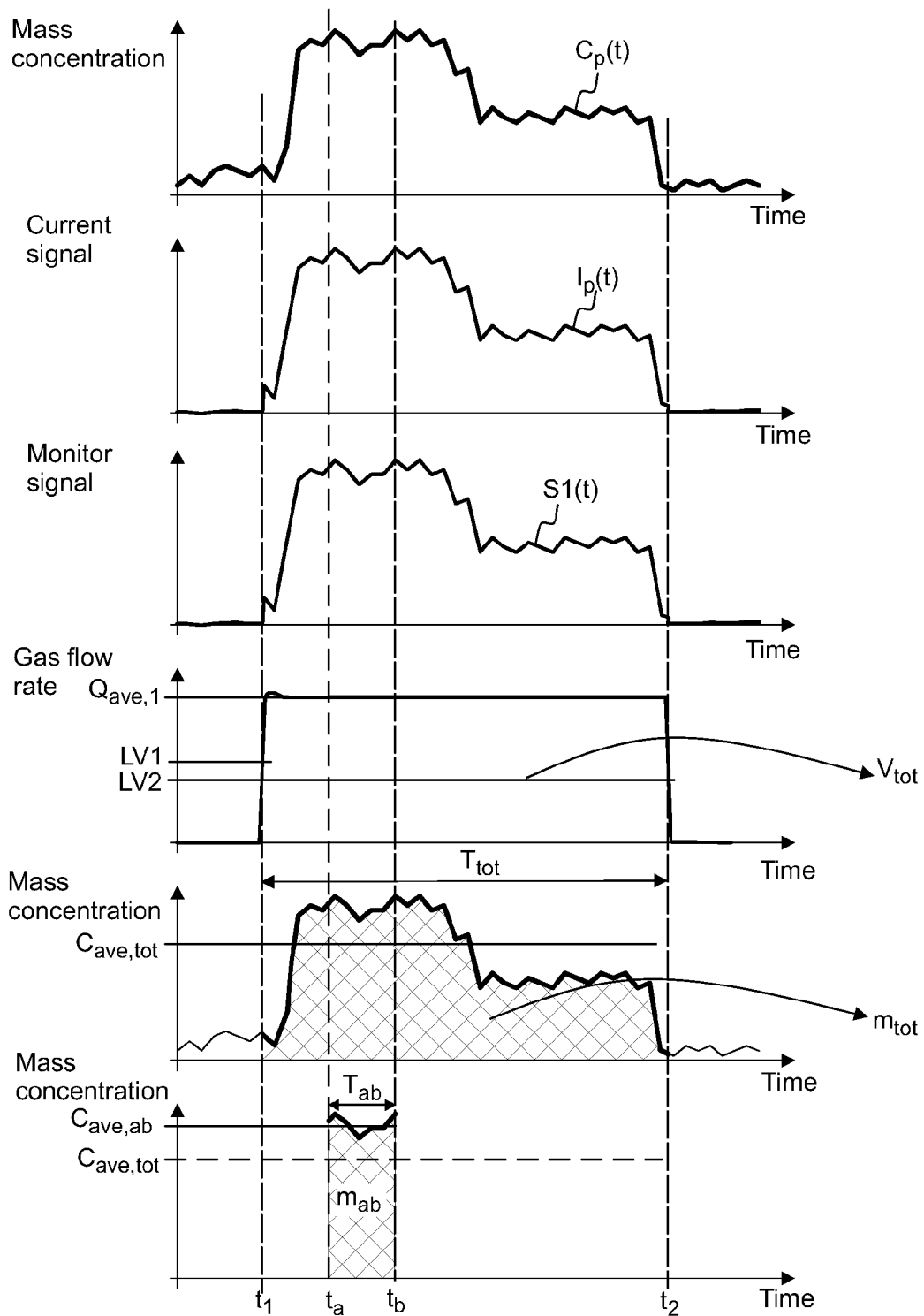
FIG. 6 shows, by way of example, formation of the measured values.

FIG. 6 illustrates, by way of example, formation of the measured signals.

The uppermost curve of FIG. 6 shows, by way of example, the temporal evolution of the concentration $C_p(t)$ of aerosol particles of the input flow FG0. $C_p(t)$ denotes the actual mass concentration. The aim of the particle measurement may be to provide one or more measured values, which represent the actual mass concentration $C_p(t)$.

The second curve from the top of FIG. 6 shows the temporal evolution of the electric current $I_p(t)$. The electric current $I_p(t)$ may be substantially proportional to the active surface area concentration of the aerosol particles of the input flow FG0. To the first approximation, the temporal variations of the active surface area concentration may provide an estimate for the temporal variations of the mass concentration $C_p(t)$.

The electric current $I_p(t)$ may also depend on the flow rate $Q_2$ of the second partial flow FG2. The electric current $I_p(t)$ may be substantially proportional to the flow rate $Q_2$. The flow rate $Q_2$ may be substantially equal to zero before the start time $t_1$ and after the stop time $t_2$. The electric current $I_p(t)$ may be substantially equal to zero before the start time $t_1$ and after the stop time $t_2$. The flow rate $Q_2$ of the second partial flow FG2 may be kept substantially constant during the measurement time period $T_{tot}$ from the start time $t_1$ and after the stop time $t_2$.

The third curve from the top of FIG. 6 shows the monitoring signal $S1(t)$ determined from the electric current $I_p(t)$. The monitoring signal $S1(t)$ may be indicative of the electric current $I_p(t)$. The monitoring signal $S1(t)$ may be substantially proportional to the electric current $I_p(t)$.

The fourth curve from the top of FIG. 6 shows temporal evolution of the gas flow rate $Q_1$ of the first partial flow FG1 through the filter FIL1. The second partial flow FG2 may be optionally started and/or stopped based on the detected flow rate $Q_1$.

The flow through the filter FIL1 may be started at a time $t_1$ and stopped at a time $t_2$. The gas flow rate through the filter FIL1, i.e. the first partial flow FG1 may be substantially constant during the time period $T_{tot}$ between the start time $t_1$ and the stop time $t_2$.

The flow FG2 through the monitor device 200 may be started when the flow rate $Q_1$ of the first partial flow FG1 increases to the first threshold value LV1. The flow FG2 through the monitor device 200 may be stopped when the flow rate $Q_1$ of the first partial flow FG1 decreases to the second threshold value LV2. The second threshold value LV2 may be equal to the first threshold value LV1, or the second threshold value LV2 may be lower than the first threshold value LV1 in order to provide hysteresis.

Alternatively, the measurement period $T_{tot}$ may have a predetermined length, and the stopping time $t_2$ may also be determined based on the starting time $t_1$ and the predetermined length $T_{tot}$.

Referring to the second curve from the bottom of FIG. 6, the total mass $m_{tot}$ of the particles collected by the filter FIL1 during the time period $T_{tot}$ may be measured by weighing the filter FIL1 after the measurement period $T_{tot}$. The total mass $m_{tot}$ may be substantially equal to the integral of the product $Q_1(t) \cdot C_p(t)$ over the time period $T_{tot}$.

$Q_{ave,tot}$ may denote the average gas flow rate of the first partial flow FG1 during the time period $T_{tot}$. The flow rate $Q_1$ through the filter FIL1 may be accurately controlled and/or measured during the time period $T_{tot}$ so that the flow rate $Q_1$ is known. The total gas volume $V_{tot}$ guided through the filter FIL1 may be determined by multiplying the known (average) gas flow rate $Q_{1,ave}$ by the length of the time period $T_{tot}$.

The average concentration $C_{ave,tot}$ representing the whole time period $T_{tot}$ may be determined by dividing the total mass $m_{tot}$ by the total gas volume $V_{tot}$.

An instantaneous concentration value $C_1(t)$ may be determined from the average concentration $C_{ave,tot}$ by using the measured current signal $I_p(t)$.

The times $t_a$ and $t_b$ may denote arbitratry times within the measurement period $T_{tot}$. An interval $T_{ab}$ may denote a time period from the first time $t_a$ to a second time $t_b$. The interval $T_{ab}$ may be shorter than the measurement period $T_{tot}$. A concentration value $C_{ab}$ representing the shorter time interval $T_{ab}$ may be determined from the average concentration $C_{ave,tot}$ by using the measured current signal $I_p(t)$.

Referring to the lowermost curve of FIG. 6, the average concentration $C_{ab}$ representing the time interval $T_{ab}$ may be determined, after weighing the filter FIL1, from the average concentration $C_{ave,tot}$ and from the measured current signal $I_p(t)$ e.g. according to the following equation:

$$C_{ab} = C_{ave,tot} \cdot \frac{t_2 - t_1}{t_b - t_a} \cdot \frac{\int_{t_a}^{t_b} I_p(t) dt}{\int_{t_1}^{t_2} I_p(t) dt} \quad (1)$$

where $t_2 - t_1$ denotes the length of the measurement time period $T_{tot}$, $t_b - t_a$ denotes the length of the interval $T_{ab}$, the upper integral denotes the integral of the electric current $I_p(t)$ over the time period $T_{ab}$, and the lower integral denotes the integral of the current signal $I_p(t)$ over the time period $T_{tot}$.

The interval $T_{ab}$ may be shorter than the measurement time period $T_{tot}$. The measurement time period $T_{tot}$ may comprise the interval $T_{ab}$, i.e. the interval $T_{ab}$ may be a sub-period of the time period $T_{tot}$. The interval $T_{ab}$ may be called as the sub-period $T_{ab}$.

An estimate $C_1(t_a)$ for the instantaneous concentration $C_p(t_a)$ at a time $t_a$ may be determined from the average concentration $C_{ave,tot}$ by using the measured electric current $I_p(t)$:

$$C_1(t_a) = \frac{I_p(t_a) \cdot (t_2 - t_1)}{\int_{t_1}^{t_2} I_p(t) dt} \cdot C_{ave,tot} \quad (2)$$

The equation (2) may be used for interpolation, i.e. the time period $T_{tot}$ may comprise the time $t_a$. The equation (2) may provide a proportionality constant for calculating the estimate $C_1(t_a)$ of the instantaneous concentration $C_p(t_a)$ from the instantaneous current value $I_p(t_a)$.

In an embodiment, an estimate $C_1(t_a)$ of the instantaneous concentration $C_p(t_a)$ may be calculated by using said proportionality constant also when the time period from the time $t_1$ to the time $t_2$ does not comprise the time $t_a$. In other words, the estimate $C_1(t_a)$ may also be calculated by extrapolation.

The mass $m_{ab}$ of particles collected by the filter FIL1 during the sub-period $T_{ab}$ may be determined from the mass $m_{tot}$ and from the measured signal $I_p(t)$ e.g. according to the following equation:

$$m_{ab} = m_{tot} \cdot \frac{\int_{t_a}^{t_b} I_p(t) dt}{\int_{t_1}^{t_2} I_p(t) dt} \quad (3)$$

The monitoring signal $S1(t)$ may be substantially proportional to the electric current signal $I_p(t)$. The electric current signal $I_p(t)$ appearing in equations (1), (2), and (3) may also be replaced with the monitoring signal SW). The average concentration $C_{ab}$ may be calculated by substituting the signal $I_p(t)$ with the monitoring signal $S_1(t)$ in equation (1). The estimate $C_1(t_a)$ may be calculated by substituting the signal $I_p(t)$ with the monitoring signal $S1(t)$ in equation (2). The mass $m_{ab}$ may be calculated by substituting the signal $I_p(t)$ with the monitoring signal $S1(t)$ in equation (3).

Figure 7:
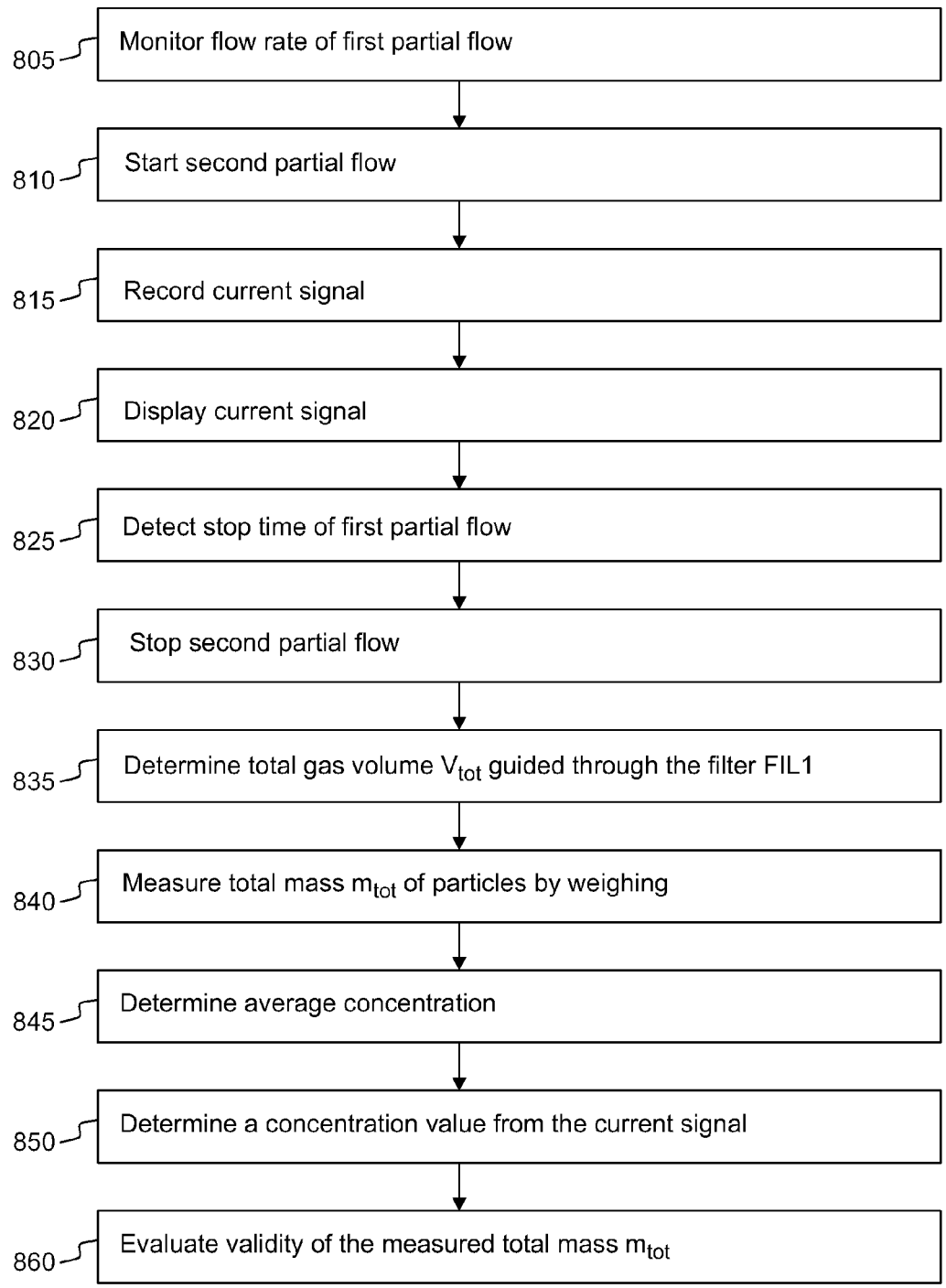
FIG. 7 shows, by way of example, method steps for operating the particle measurement apparatus.

FIG. 7 shows, by way of example, method steps for operating the measurement apparatus 500. The second partial flow FG2 to the monitoring device 200 may be controlled based on the flow rate $Q_1$ guided through the collecting unit 100.

Monitoring of the flow rate $Q_1$ of the first partial flow FG1 may be started in step 805.

The second partial flow FG2 may be started e.g. when the flow rate $Q_1$ increases to the threshold value LV1 (step 810).

The electric current $I_p(t)$ may be measured in step 815. The magnitude of the electric current $I_p(t)$ may be optionally displayed in step 820. The magnitude of the electric current $I_p(t)$ may be displayed e.g. by displaying a curve on a display.

The second partial flow FG2 may be stopped e.g. when the flow rate $Q_1$ decreases to the threshold value LV2 (step 825).

The total gas volume $V_{tot}$ guided through the filter FIL1 may be determined in an optional step 835. The total gas volume $V_{tot}$ may be determined e.g. determined based on the known flow rate $Q_1$, based on the known start time $t_1$ and based on the known stop time $t_2$.

The total mass $m_{tot}$ of particles collected by the filter FIL1 may be determined by weighing the filter FIL1 in step 840.

In an optional step 845, the average concentration $c_{tot,ave}$ of the particles may be calculated by dividing the total mass $m_{tot}$ by the total gas volume $V_{tot}$.

In an optional step 850, the average concentration $C_{ab}$, the estimate $C_1(t_a)$ of the instantaneous concentration, and/or the mass $m_{ab}$ may be calculated from the measured current signal $I_p(t)$ and from the total mass $m_{tot}$.

In an optional step 860, the validity of the measured total mass $m_{tot}$ may be determined.

The apparatus 500 may provide measurement data, which may be used for analysis of particle emission from an engine or from an industrial process. The particle emission may be associated with serious economic and/or environmental consequences. The signals recorded in the memory of the apparatus 500 may be optionally protected against tampering and/or erasing. The signals recorded in the memory MEM1 may be protected e.g. by one or more credentials provided by a user. The credentials may comprise e.g. a password, an RFID key, and/or a biometric indicator. RFID means radio frequency identification. The apparatus 500 may be arranged to operate such that altering or erasing the recorded data causes writing an additional record in a register of the apparatus. The additional record may comprise e.g. the time of altering the data and the identity of the user who altered the data. The identity of the user may be determined e.g. based on the password or RFID identification.

The continuous monitoring may be synchronized with the operation of the filter. For example, the continuous monitoring may be started when the gas flow FG1 guided through the filter FIL1 is started, and/or the continuous monitoring may be stopped when the gas flow to the filter is stopped. The apparatus may comprise a flow rate sensor SEN1 for detecting when the gas flow guided through the filter is started and/or stopped. The continuous monitoring may be controlled based on the gas flow FG1 of the particle collecting unit. The apparatus 500 may be arranged to start operation of the monitor device 200 when collecting of particles by the collecting unit 100 is started. The apparatus 500 may be arranged to stop operation of the monitor device 200 when collecting of particles by the collecting unit 100 is stopped. The apparatus 500 may be arranged to control operation of the pump PUMP2 and/or to control operation of the valve 280 based on the flow rate $Q_1$ of the first partial flow FG1. The apparatus 500 may be arranged to start operation of the pump PUMP2 and/or to open a control valve 280 when the flow rate $Q_1$ of the first partial flow FG1 becomes higher than a first threshold value (i.e. after the flow rate $Q_1$ has been at a lower value). The apparatus 500 may be arranged to stop operation of the pump PUMP2 and/or to close a control valve 280 when the flow rate $Q_1$ of the first partial flow FG1 becomes lower than a second threshold value (after the flow rate $Q_1$ has been at a higher value). The apparatus 500 may be arranged to control operation of the monitor device 200 based on the flow rate $Q_1$ or internal pressure of the collecting unit 100 downstream the filter FIL1. The apparatus 500 may comprise a flow rate sensor SEN1 for monitoring the flow rate of the first partial flow FG1 and/or the apparatus 500 may comprise a pressure sensor SEN1 to monitor the gas pressure downstream the filter FIL1. The flow rate sensor and/or the pressure sensor may provide a flow rate signal. The apparatus 500 may be arranged to control operation of the monitor device 200 based on the flow rate signal. Controlling operation of the monitor device 200 based on the flow rate signal may provide e.g. one or more of the following advantages: energy consumption of the monitor device 200 may be minimized, lifetime of the monitor device 200 may be maximized, and/or the contamination of the monitor device 200 may be minimized.

The monitoring device 200 may be used for checking the validity of the measured total mass of particles. A measurement performed in certain operating conditions may be performed again if the validity check indicates that the measured total mass of particles is invalid.

The device 500 may be used e.g. for measuring particle emissions from an engine SRC1. The engine may be driven according to first test procedure. The first test procedure may comprise e.g. adjusting a control signal of the engine (e.g. the gas pedal position), and/or the load of the engine (i.e. the output power) according to a predetermined sequence. The method may comprise obtaining a process indicator signal P(t) indicative of an operating parameter of the engine SRC1. The operating parameter of the engine SRC1 may be e.g. fuel consumption, speed of rotation, power control signal (gas pedal position), or output power.

The method may comprise:
- operating an engine SRC1 according to a first test procedure during a first test period $T_{tot,1}$,
- collecting particles P1 from the exhaust gas PG0 of the engine SRC1 to a first filter FIL1 during a first test period $T_{tot,1}$,
- obtaining a process indicator signal P(t) indicative of an operating parameter of the engine SRC1, and
- determining whether the electric current signal $I_p(t)$ measured during the first test period $T_{tot,1}$ substantially corresponds to the process indicator signal P(t) obtained during the first test period $T_{tot,1}$.

Said determining may comprise e.g. checking whether a change of the electric current signal $I_p(t)$ temporally coincides with a change of the process indicator signal P(t).

Said determining may comprise e.g. checking whether at least one change of the electric current signal $I_p(t)$ temporally coincides with at least one change of the process indicator signal P(t).

Said determining may comprise e.g. calculating a cross correlation between the electric current signal $I_p(t)$ and the process indicator signal P(t).

Collecting particles to the first filter FIL1 may be interrupted if the electric current signal $I_p(t)$ measured during the first test period $T_{tot,1}$ does not correspond to the process indicator signal P(t) obtained during the first test period $T_{tot,1}$.

The method may comprise performing an additional measurement after the first test period $T_{tot,1}$ if the electric current signal $I_p(t)$ measured during the first test period $T_{tot,1}$ does not correspond to the process indicator signal P(t) obtained during the first test period $T_{tot,1}$. Said performing may comprise operating the engine SRC1 according to the first test procedure during a second test period $T_{tot,2}$, and collecting particles P1 from the exhaust gas PG0 of the engine SRC1 to a second filter FIL2 during the second test period $T_{tot,2}$.

The total volume of gas guided through the filter during the particle collecting period may be calculated based on the flow rate of the first partial flow. The total mass of particles collected by the filter may be determined e.g. by weighing the filter before and after collecting the particles.

Manual or automatic handling of the filter may cause various types of measurement errors. The measured change of the weight of the filter FIL1 may be smaller than the mass of particles collected by the filter FIL1 e.g. if a part of the collected particles fall away from the filter before weighing. The measured change of the weight of the filter FIL1 may be smaller than the mass of particles collected by the filter FIL1 e.g. due to evaporation of material away from the filter FIL1. The measured change of the weight of the filter FIL1 may be higher than the mass of particles collected by the filter FIL1 e.g. due to subsequent contamination of the filter FIL1. The measured change of the weight of the filter FIL1 may be higher than the mass of particles collected by the filter FIL1 e.g. due to condensation of material on the filter FIL1.

One or more measurement results may be determined from the collected particle sample. The particle sample collected by the filter FIL1 may be weighed and/or analyzed. The filter FIL1 may be weighed in order to measure the weight of the particles collected by the filter FIL1. For example, the chemical composition of the particle sample may be determined by chemical analysis. For example, the structure of the particles of the article sample may be determined by using a scanning electron microscope (SEM) or by using a transmission electron microscope (TEM).

Analysis of the monitoring signal S1(t) may indicate e.g. whether the particle concentration varied significantly during a particle collecting period. One or more characteristic values may be determined from a monitoring signal S1(t) provided by the monitor device 200. For example a temporally integrated value may be determined from the monitoring signal S1(t). For example a temporally averaged value may be determined from the monitoring signal S1(t). For example, a characteristic value may indicate an average rate of change of the monitoring signal S1(t). For example, a characteristic value may indicate a maximum rate of change of the monitoring signal S1(t).

The recorded monitoring signal S1(t) may be provided such that one or more characteristic values of the recorded monitoring signal S1(t) may be associated with one or more measurement results determined from the collected particle sample.

Figure 8A:
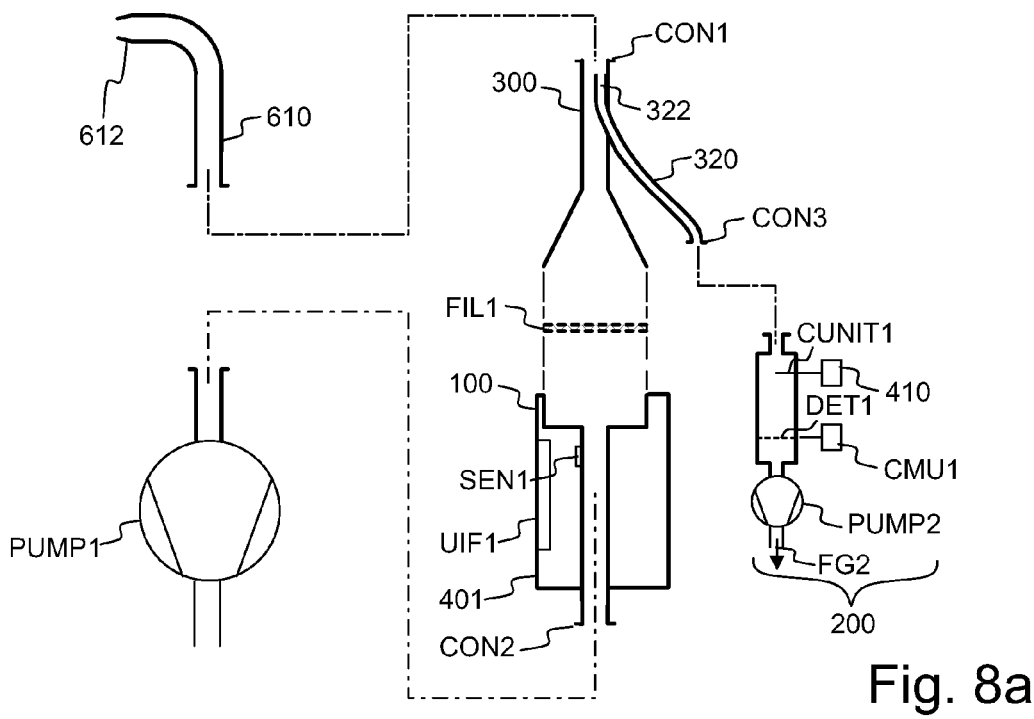
FIG. 8a shows, by way of example, units of a disassembled measurement system.
Figure 8B:
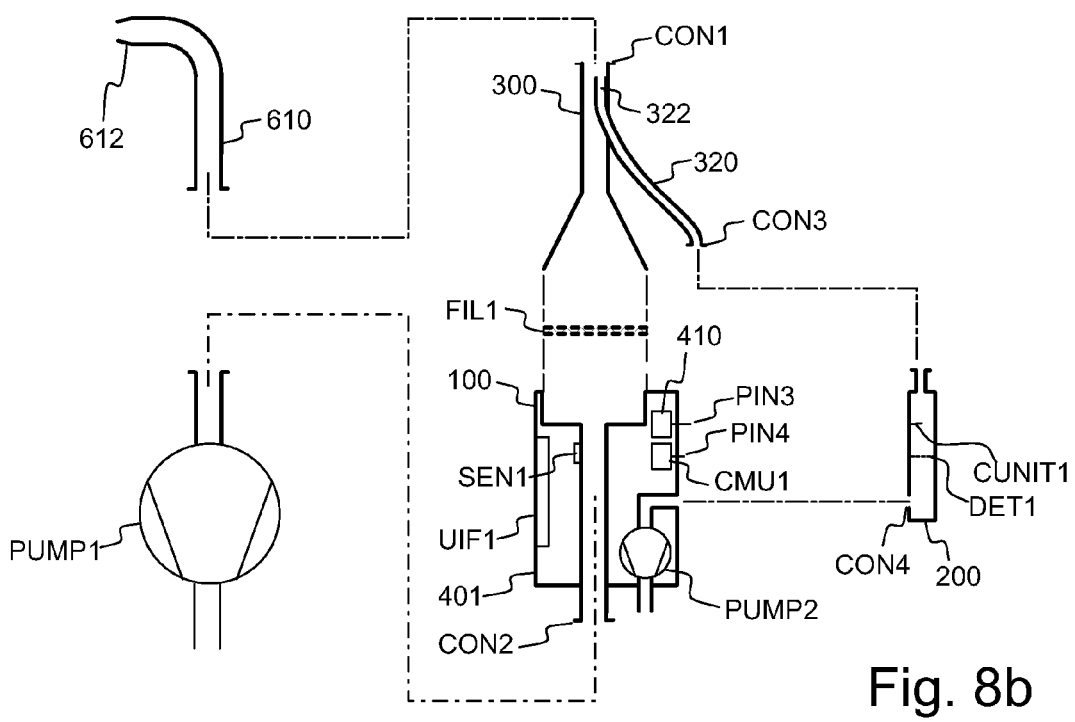
FIG. 8b shows, by way of example, units of a disassembled measurement system.
Figure 8C:
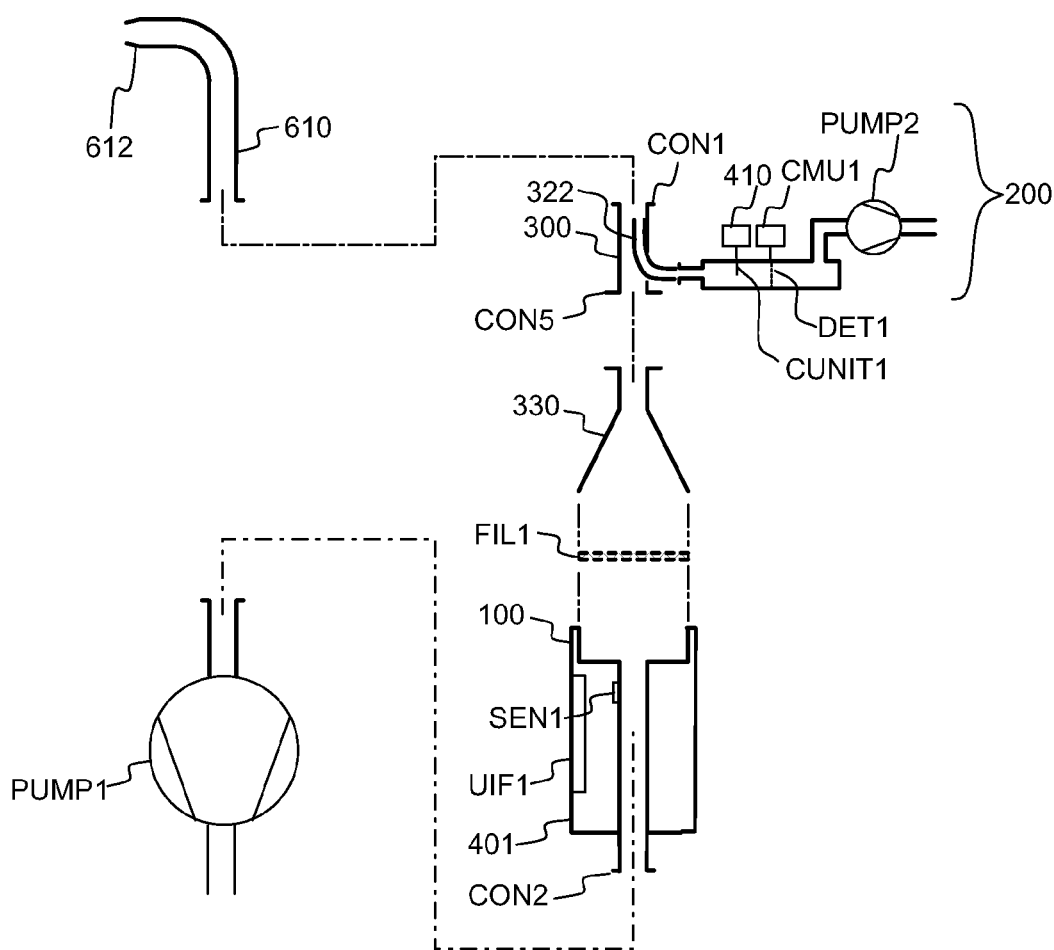
FIG. 8c shows, by way of example, units of a disassembled measurement system.

FIGS. 8a-8c show, by way of example, how the units 100, 200, 300 of the aerosol measuring apparatus 500 may be separated from each other in order to replace the filter FIL1 and/or in order to replace the monitoring unit 200. Preparations for a measurement may comprise e.g. replacing the filter FIL1 and/or replacing the monitoring device 200. The filter FIL1 may be replaceable and/or disposable part. The filter FIL1 may be provided separately, and the filter FIL1 may be positioned to the filter holder of the apparatus 500 before the particle collecting period. After the particle collecting period, the filter FIL1 may be removed from the apparatus 500 for subsequent weighing.

Referring to FIG. 8a, the monitoring device 200 may be separated from the distributor 300 in order to replace the monitoring unit. The collecting unit 100 may be separated from the distributor 300 in order to replace the filter FIL1.

Referring to FIG. 8b, the high voltage supply 410, the current monitoring unit CMU1, the control unit CNT1, a user interface UIF1, a battery BAT1, and/or the pump PUMP2 may be attached to the frame 401. The monitoring device 200 may be separated from the distributor 300 e.g. by opening the connectors CON3 and CON4. The apparatus 500 may comprise a connecting element PIN3 for connecting the corona electrode ELEC3 to the high voltage supply 410. The apparatus 500 may comprise a connecting element PIN4 for connecting the detector DET1 to the current monitoring unit CMU1.

Referring to FIG. 8c, the monitoring device 200 may be removably or permanently attached to the distributor 300. The monitoring device 200 may be attached to the side of the distributor 300. The first partial flow FG1 may be guided from the distributor 300 to the filter FIL1 through an extension unit 330. The distributor 300 may be separated from an extension unit 330 e.g. by opening a connector CON5. The filter FIL1 may be replaced by separating the extension unit 330 from the collecting unit 100.

Figure 9A:
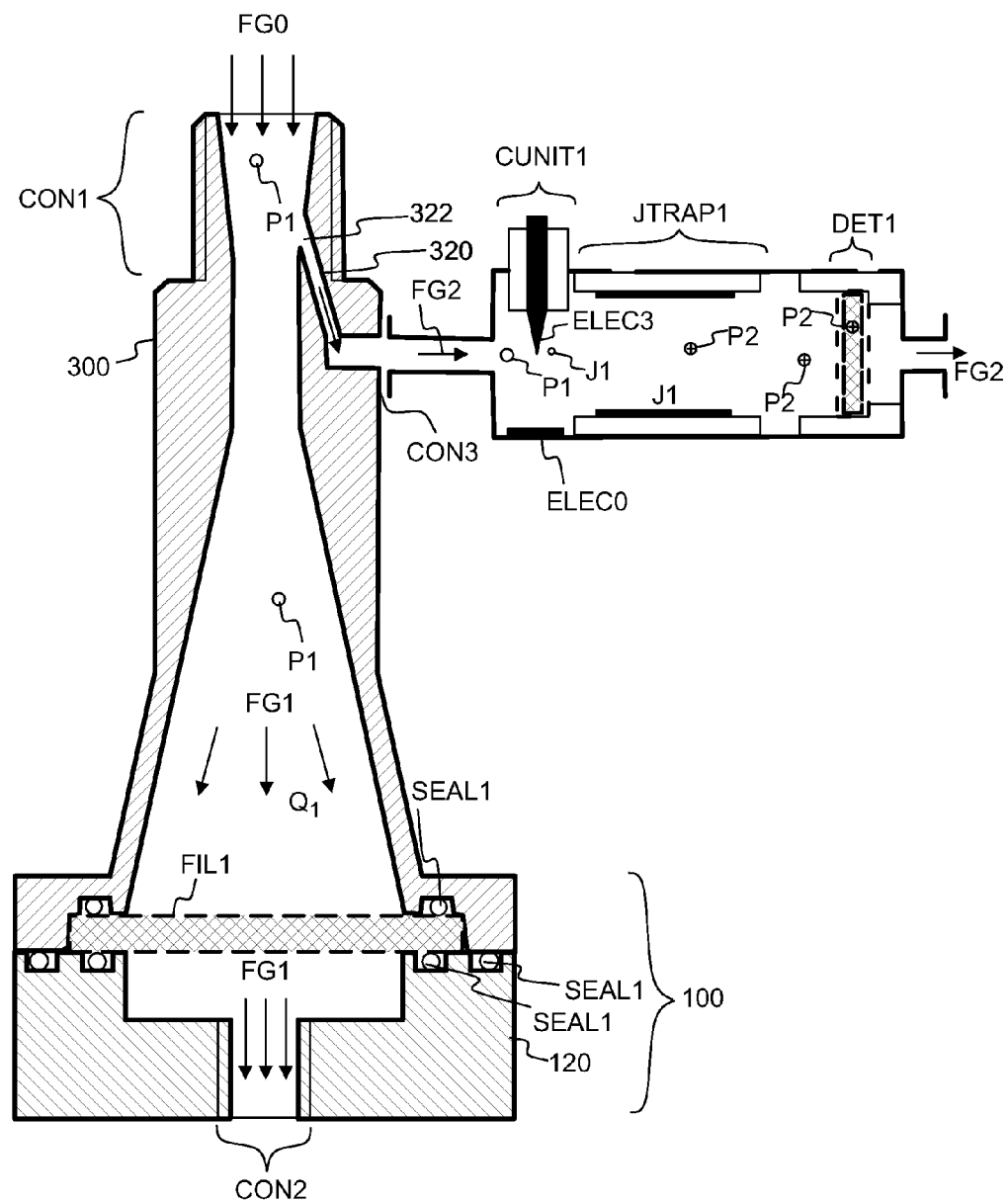
FIG. 9a shows, by way of example, a distributor where the sampling nozzle does not protrude with respect to the inner wall of the flow channel.
Figure 9B:
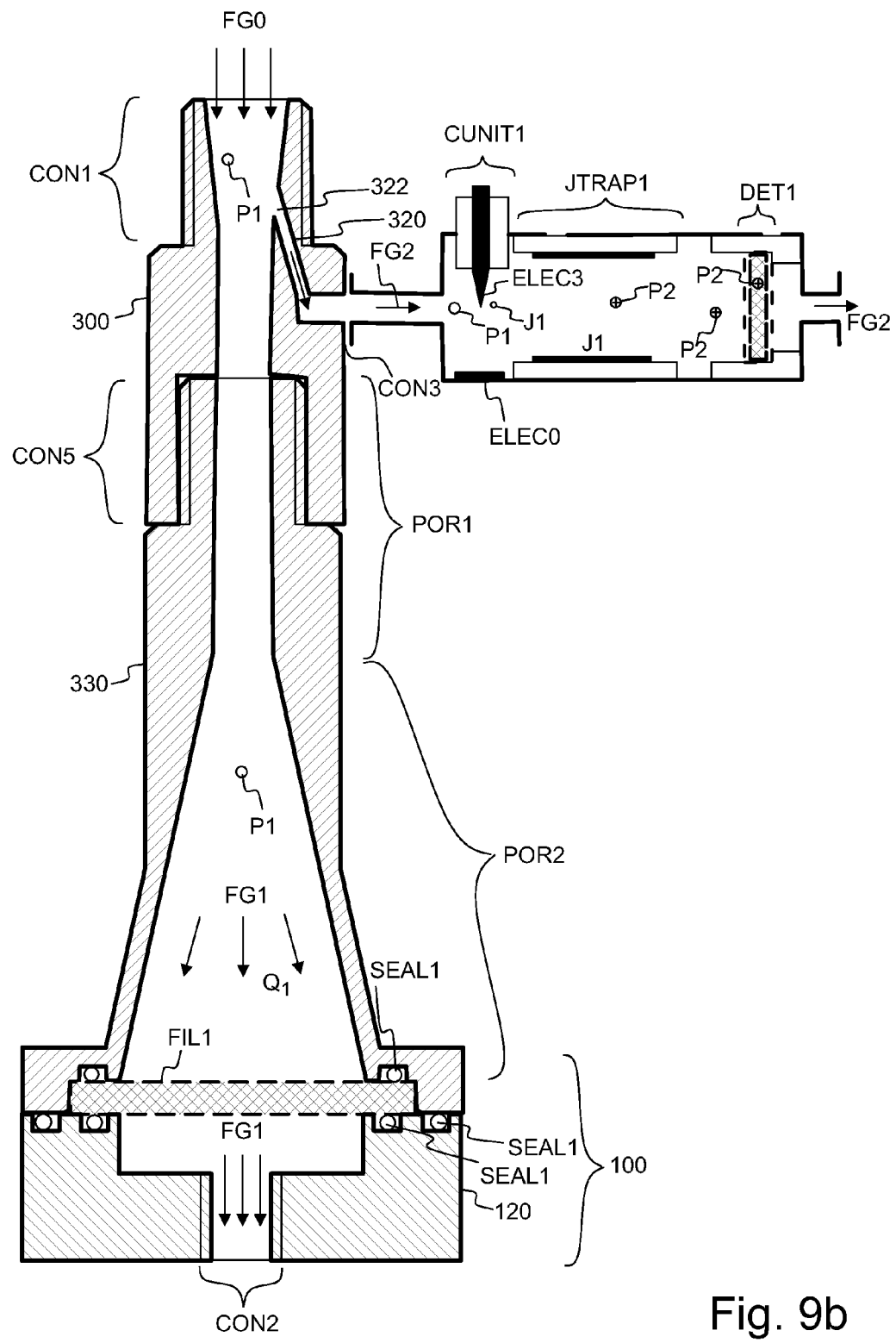
FIG. 9b shows, by way of example, in a cross-sectional side view, an extension unit which is removably attached to the distributor

Referring to FIG. 9a, the secondary sampling nozzle 322 may also be substantially flush which the inner surface of the primary duct 310. The protrusion of the secondary sampling nozzle 322 with respect to the inner surface of the primary duct 310 may be substantially equal to zero.

The length of the secondary duct 320 may be small. The monitoring device 200 may be removably or permanently attached to the side of the distributor 300. The monitoring device 200 may even be integrated in the distributor 300.

Referring to FIG. 9b, the primary duct 310 may be implemented by using two or more parts. The apparatus 500 may comprise an extension unit 330, which may be removably attached to the distributor 300. The first partial flow FG1 may be guided from the distributor 300 to the filter FIL1 through the extension unit 330. The extension unit 330 may comprise the portions POR1, POR2. The combination of the distributor 300 and the extension unit 330 may comprise the portions POR1, POR2. The distributor 300 and an extension unit 330 may together form the primary duct 310 for guiding the primary flow FG1 to the filter FIL1. The distributor 300 and the extension unit 330 may together form a primary duct 310, which has the straight portion POR1 and the conically diverging portion POR2. The extension unit 330 may be removably attached to the distributor 300.

Figure 10A:
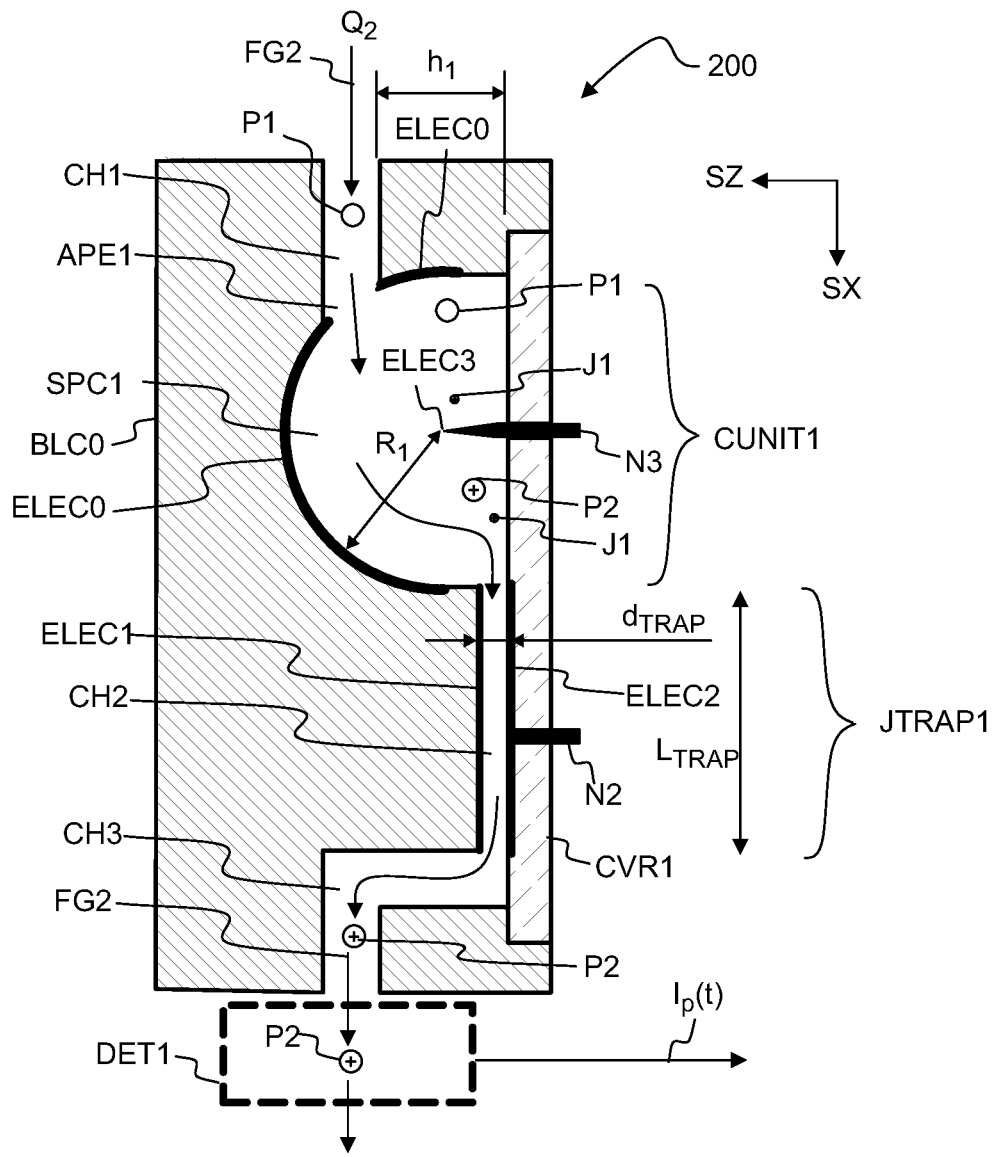
FIG. 10a shows, by way of example, in a cross-sectional view, a particle monitoring device of the particle measuring apparatus.

Referring to FIG. 10a, the charging unit CUNIT1 of the monitoring device 200 may have a corona electrode ELEC3 and a counter-electrode ELEC0. The charging unit CUNIT1 may comprise a charging space SPC1 defined by the electrodes ELEC0, ELEC3. The charging space SPC1 may also be called e.g. as the charging volume or as the charging zone. The gas flow FG2 and neutral particles P1 may be guided into the charging space SPC1 via an inlet channel CH1. The gas flow FG2 and charged particles P2 may be guided from the charging space SPC1 via an outlet channel CH2.

The corona electrode ELEC3 and the counter-electrode ELEC0 may together define a substantially hemispherical charging space SPC1. The counter-electrode ELEC0 may be substantially hemispherical. The counter-electrode ELEC0 may have a portion, which is substantially hemispherical. The counter-electrode ELEC0 may have a substantially spherical surface to define a hollow half of a sphere. The corona electrode ELEC3 may be a conductive element which has an exposed sharp tip. The tip of the corona electrode ELEC3 may be located at an axis of symmetry of the hemispherical charging space SPC1. The distance between the tip and each point of the hemispherical portion of the electrode ELEC0 may be substantially equal to $R_1$. The charging of the particles may take place in the charging space SPC1 between the corona electrode ELEC3 and the counter-electrode ELEC0.

The shape of the corona electrode ELEC3 may change during operation due to electrode erosion. The substantially hemispherical charging space SPC1 may provide a symmetric electric field, which in turn may facilitate maintaining the symmetrical shape of the corona electrode ELEC3 during operation. The substantially hemispherical charging space SPC1 may reduce or minimize electrical power needed for generating the corona discharge. The hemispherical charging space may e.g. reduce the effect of a change of temperature on the degree of charging of the particles. The hemispherical charging space may e.g. reduce the effect of a change of gas flow rate on the degree of charging of the particles. The hemispherical charging space may help to provide sufficient gas velocity in the vicinity of the surfaces of the charging space, so as to minimize deposition of particles to said surfaces. The hemispherical shape may reduce the residence times of the particles in the charging space SPC1. The hemispherical shape may facilitate providing a fast response time. The particles may travel through the charging space SPC1 along different paths. A first path may be close to the corona electrode ELEC3. A second path may be close to the counter electrode ELEC0. The density of ions J1 close to the corona electrode ELEC3 may be higher than the density of ions J1 close to the counter electrode ELEC0. Particles traveling along the first path may have a shorter residence time in the charging space SPC1 but they may be exposed to a higher ion density. Particles traveling along the second path may have a second longer residence time in the charging space SPC1 but they may be exposed to a lower ion density. Thus, the hemispherical shape may reduce the effect of the different paths on the final degree of charging of the charged particles P2.

The counter-electrode ELEC0 may be substantially impermeable to the gas in order to define the gas flow passing through the charging space SPC1. The counter-electrode ELEC0 may be substantially impermeable to the gas of the gas flow FG2 in order to ensure that substantially all particles of the gas flow FG2 pass from the channel CH1 to the channel CH2 through the charging space SPC1. The outlet channel CH2 may be e.g. substantially parallel with the inlet channel CH1.

The counter-electrode ELEC0 may have an inner radius $R_1$. The substantially hemispherical portion of the counter-electrode ELEC0 may comprise an opening APE1 for guiding the flow FG2 from the inlet channel CH1 to the charging space SPC1. The substantially hemispherical counter-electrode ELEC0 may define the opening APE1 for guiding the flow FG2 from the inlet channel CH1 to the charging space SPC1. The flow FG2 may pass from the inlet channel CH1 to the charging space SPC1 via the opening APE1 of the counter-electrode ELEC0. The dimension $h_1$ may denote the distance between the opening APE1 and the planar portion of the boundary of the hemispherical charging space SPC1. The distance $h_1$ may be e.g. greater than 0.3 times the inner radius $R_1$ in order to prevent a straight travel path of particles through the charging space SPC1.

The corona electrode ELEC3 may have a substantially sharp tip. The radius of curvature of the tip may be e.g. smaller than 0.2 mm. The distance between the tip of the corona electrode ELEC3 and the counter-electrode ELEC0 may be substantially equal to $R_1$.

The gas flow FG2, the charged particles P2, and the ions J1 may be guided from the charging space SPC1 into the ion trap JTRAP1. The ion trap JTRAP1 may be located between the charging space SPC1 and the detector DET1. The gas flow FG2 and the charged particles P2 may be guided from the ion trap JTRAP1 to the detector DET1.

The ion trap JTRAP1 may comprise a first deflecting electrode ELEC1 and a second deflecting electrode ELEC2. The deflecting electrodes ELEC1, ELEC2 may together form an electric field, which deflects at least part of the ions J1 away from the gas flow FG2. $d_{TRAP}$ may denote the distance between the electrodes ELEC1, ELEC2. $L_{TRAP}$ may denote the length of the ion trap JTRAP1.

The radial distance $R_1$ between the electrodes ELEC3, ELEC0 may be e.g. in the range of 1 mm to 50 mm, advantageously in the range of 2 mm to 20 mm, and preferably in the range of 3 mm to 10 mm. Using a small distance $R_1$ may provide more effective charging of the particles P2. The voltage difference $U_C-U_0$ applied between the electrodes ELEC3, ELEC0 may be reduced when using a small distance $R_1$. However, the charging space SPC1 may be clogged or short-circuited by a particle P2 if the distance $R_1$ is very small.

The distance $d_{TRAP}$ between the deflecting electrodes ELEC1, ELEC2 may be e.g. in the range of 0.1 mm to 2 mm, advantageously in the range of 0.2 mm to 1.0 mm, and preferably in the range of 0.3 mm to 0.8 mm. The distance $d_{TRAP}$ may be e.g. smaller than 20% of the radius $R_1$. The voltage difference $U_2-U_1$ applied between the deflecting electrodes ELEC1, ELEC2 may be reduced when using a small distance $d_{TRAP}$. However, the channel CH2 may be clogged or short-circuited by a particle P2 if the distance $d_{TRAP}$ is very small. The length $L_{TRAP}$ may be e.g. in the range of 2 mm to 50 mm.

The deflecting electrodes ELEC1, ELEC2 may be e.g. substantially planar. The deflecting electrodes ELEC1, ELEC2 may together define a flow channel CH2. The flow channel CH2 may receive the gas flow FG2, charged particles P2, and ions J1 from the charging space SPC1. The input of the flow channel CH2 may be located close to the charging space SPC1. The input of the flow channel CH2 may be located close to a planar portion of the hemispherical charging space SPC1. The distance between the electrode ELEC2 and the corona electrode ELEC3 may be e.g. smaller than 1.2 times the radius $R_1$.

The gas flow FG2 and the charged particles P2 may be guided from the ion trap JTRAP to the particle detector DET1 via a channel CH3. The particle detector DET1 may provide the electric current signal $I_p(t)$, which may be substantially equal to the charge captured by the particle detector DET1 per unit time.

The counter-electrode ELEC0 and/or the deflecting electrode ELEC1 may be at the same electric potential. The counter-electrode ELEC0 and/or the deflecting electrode ELEC1 may be at the ground potential $U_0$. The deflecting electrode ELEC1 may be galvanically connected to the counter-electrode ELEC0. The counter-electrode ELEC0 and/or the deflecting electrode ELEC1 may be implemented on the surface of a body BLC0. The counter-electrode ELEC0 and/or the deflecting electrode ELEC1 may be implemented on the surface of a conductive body BLC0. The counter-electrode ELEC0 and/or the deflecting electrode ELEC1 may be formed e.g. from a single metal block by mechanical machining. The counter-electrode ELEC0, the deflecting electrode ELEC1, the inlet channel CH1, and the outlet channel CH2 may be formed from a single metal block by mechanical machining. This may provide an extremely rugged and stable structure. The counter-electrode ELEC0 and/or the deflecting electrode ELE3 may also be formed e.g. by molding or 3D printing. The counter-electrode ELEC0 and/or the deflecting electrode ELE3 may be formed e.g. by depositing conductive material on electrically insulating material.

The corona electrode ELEC3 and/or the deflecting electrode ELEC2 may be supported by a supporting element CVR1. The supporting element CVR1 may be electrically insulating. The supporting element CVR1 may also be called e.g. as the cover of the charging space SPC1. The electrode ELEC0 and/or ELEC1 may be galvanically connected to a contact surface N1. The corona electrode ELEC3 may be galvanically connected to a contact element N3. The deflecting electrode ELEC2 may be galvanically connected to a contact element N2. The electrodes ELEC2, ELEC3 may be on a first side of the cover CVR1, and the elements N2, N3 may be on a second side of the cover CVR1. The elements N2, N3 may also extend through the cover CVR1 from the first side to the second side. The elements N3, N2 may be e.g. metallic stubs. The planar surface of the electrically insulating cover CVR1 may partly define the hemispherical form of the charging space SPC1. The cover CVR1 may have a substantially planar surface, which may partly define the charging space SPC1. The substantially planar surface of the cover CVR1 may partly define the hemispherical charging space SPC1.

The cover CVR1 may also support the deflecting electrode ELEC2. A planar surface of the cover CVR1 may support the deflecting electrode ELEC2. The deflecting electrode ELEC2 may be substantially parallel with the planar portion of the charging space SPC1. The electrode ELEC2 may be implemented e.g. by depositing conductive material on the surface of the cover CVR1, or by attaching a conductive foil on the surface of the cover CVR1.

The planar surface of the deflecting electrode ELEC2 may partly define the flow channel CH2. The cover CVR1 may form a pressure-tight seal together with the body BLC0. The cover CVR1 may electrically insulate the corona electrode ELEC3 from the conductive body BLC0. The cover CVR1 may electrically insulate the deflecting electrode ELEC2 from the conductive body BLC0.

Using the planar electrodes ELEC1, ELEC2 may provide a simple and rugged structure. In an embodiment, the ion trap JTRAP may also be implemented by using non-planar electrodes ELEC1, ELEC2, e.g. by using a pair of concentric electrodes. The electrodes ELEC1, ELEC2 may be e.g. concentric cylindrical electrodes.

SX, SY and SZ denote orthogonal directions.

Figure 10B:
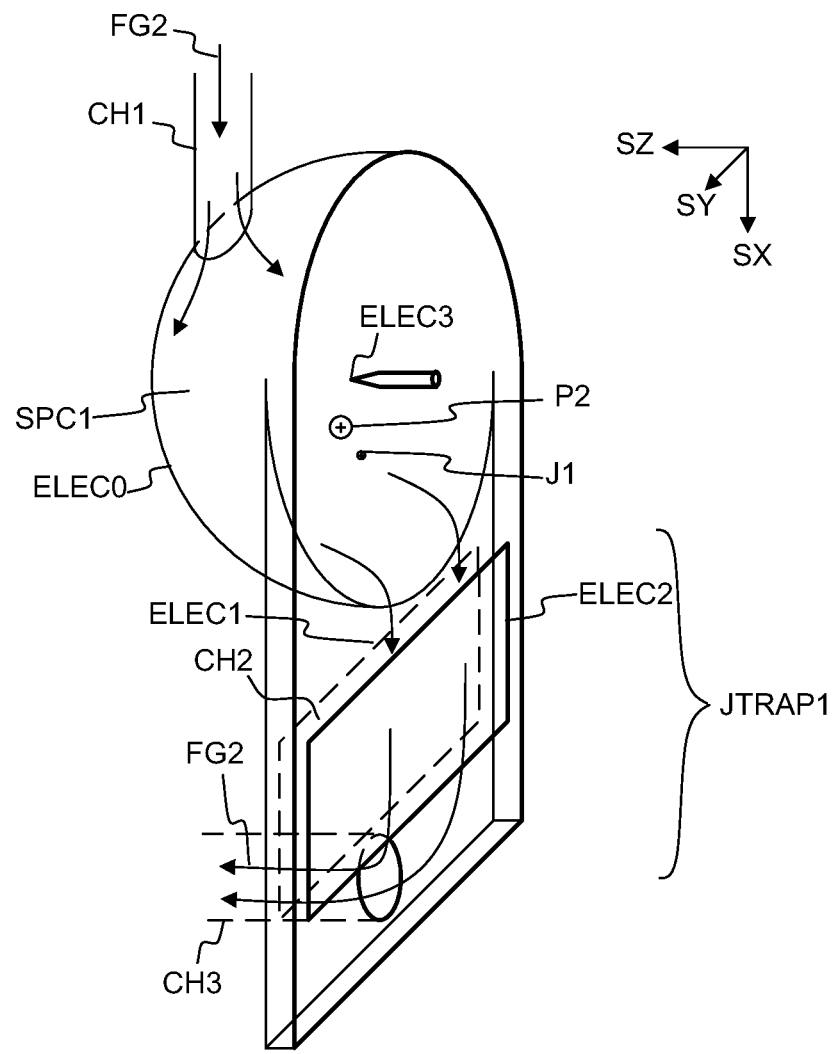
FIG. 10b shows, by way of example, in a three-dimensional view, a charging space and an ion trap for the particle monitoring device.

FIG. 10b shows, in a three dimensional view, the hemispherical charging space SPC1 and the ion trap JTRAP1.

Figure 10C:
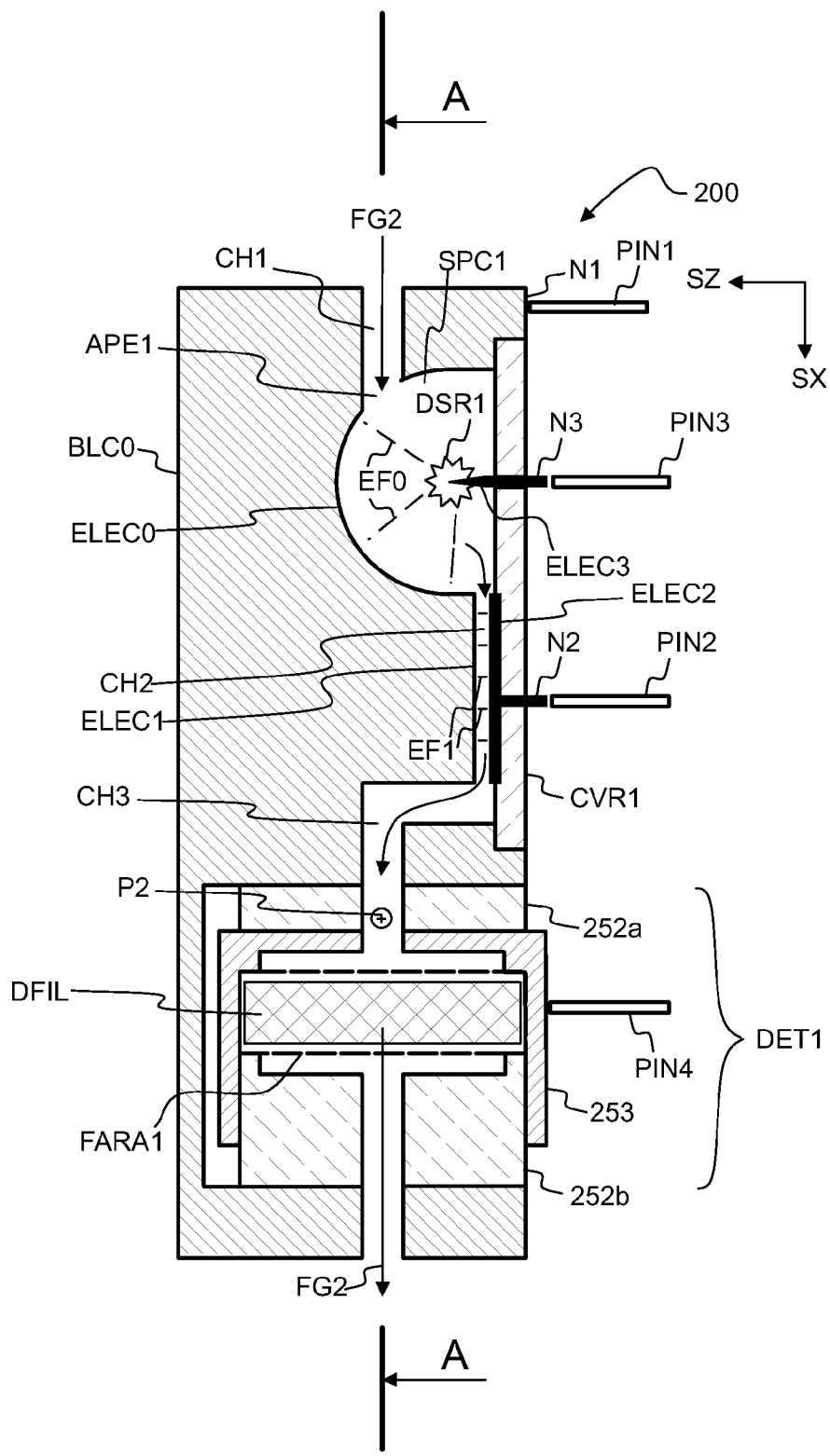
FIG. 10c shows, by way of example, in a cross-sectional view, a particle monitoring device.
Figure 10D:
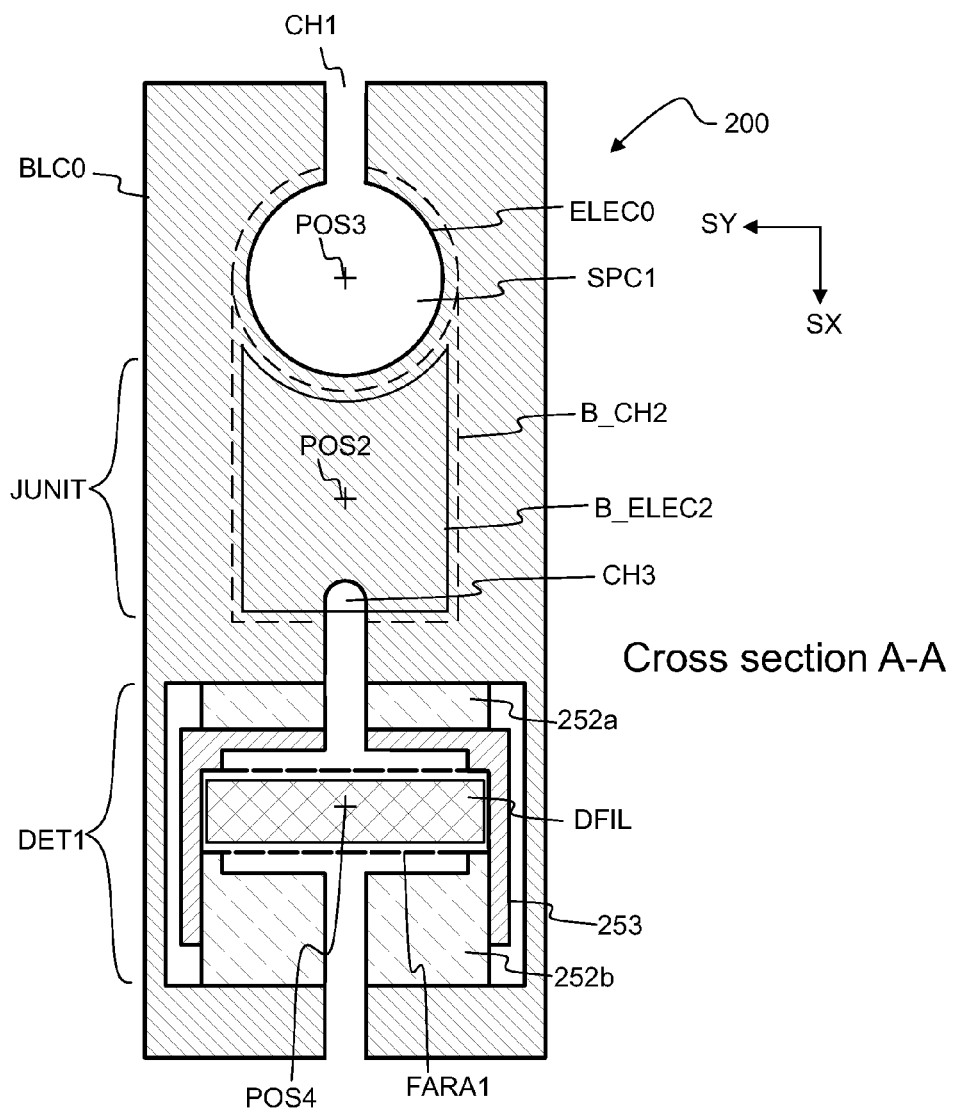
FIG. 10d shows, by way of example, a cross-section of the particle monitoring device shown in FIG. 10c.
Figure 10E:
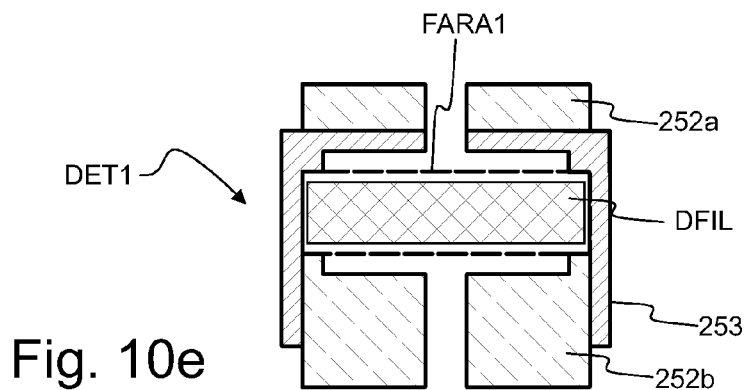
FIG. 10e shows, by way of example, in a cross-sectional view, a detector of the particle monitoring device.

Referring to FIGS. 10c and 10e, the particle detector DET1 may comprise a particle filter DFIL surrounded by a Faraday cage FARA1. The Faraday cage FARA1 may be supported by one or more electrical insulators 252a, 252b. The electrical insulators 252a, 252b may electrically insulate the Faraday cage FARA1 from the surrounding conductive structures. In particular, the electrical insulators 252a, 252b may electrically insulate the Faraday cage FARA1 from the conductive body BLC0. The one or more electrical insulators 252a, 252b may form a pressure-tight seal between the detector DET1 and the outlet channel CH3 of the ion trap JTRAP1. The detector DET1 may optionally comprise a conductive shell 253. The conductive shell 253 may form a part of the Faraday cage FARA1. The particle filter DFIL may be electrically insulating or electrically conductive. The particles P2 may be captured by the particle filter DFIL.

The particle monitoring device 200 may comprise one or more connecting elements PIN1, PIN2, PIN3, PIN4 for forming a galvanic connection with the electrodes ELEC0, ELEC1, ELEC2, ELEC3, and the detector DET1. The element PIN1 may form a galvanic contact with the electrodes ELEC0 and ELEC1. The element PIN2 may form a galvanic contact with the electrode ELEC2. The element PIN3 may form a galvanic contact with the corona electrode ELEC3. The element PIN4 may form a galvanic contact with the Faraday cage FARA1 of the detector DET1. The element PIN1 may be arranged to contact the contact element N1. Also portion of the surface of the body BLC0 may operate as the contact element N1. The element PIN2 may be arranged to contact the contact element N2. The element PIN3 may be arranged to contact the contact element N3. The connecting element PIN4 may be arranged to contact the detector DET1. The connecting elements PIN2, PIN3, PIN4 may be e.g. spring-loaded conductive pins.

FIG. 10d shows a cross-section of the particle monitoring device 200 along the line A-A shown in FIG. 3a. POS3 denotes the position of the corona electrode ELEC3. POS2 denotes the position of a contact element N2. POS4 denotes the position of a connecting element PIN4. B_CH2 denotes the position of the flow channel CH2. B_ELEC2 denotes the position of the deflecting electrode ELEC2.

FIG. 10e shows a detector DET1 when it has been separated from the device 200.

FIG. 10f shows a side view of the particle monitoring device 200. The deflecting electrode ELEC2 may be located on the inner side of the cover CVR1. The deflecting voltage $U_2$ may be coupled to the electrode ELEC2 by using the contact element N2.

The apparatus 500 may comprise a frame 401, which may support the connecting elements PIN1, PIN2, PIN3, PIN4. The monitoring device 200 may be installed to the frame 401 such that electrical connections are formed between the electrodes ELEC2, ELEC3 and the connecting elements PIN2, PIN3. However, sometimes the connection between the elements N2 and PIN2 may fail. The particle monitoring device 200 may optionally comprise an auxiliary contact element N2b for checking whether the device 200 is properly installed to the frame 401. The contact element N2b may be e.g. permanently connected to the element N2 or to the body BLC0.

FIG. 10g shows the outer side of the cover CRV1. The deflecting electrode ELEC2 may have a curved edge so that the shape of the electrode ELEC2 may match with the shape of the hemispherical charging space SPC1. The radius of curvature of the edge of the electrode ELEC2 may be substantially equal to the radius $R_1$. The radius of curvature of the edge of the electrode ELEC2 may be e.g. in the range of 0.9 to 1.1 times the radius $R_1$. The curved edge may improve the efficiency of the ion trap JTRAP1, may stabilize operation of the ion trap JTRAP1, and/or may help to reduce the outer dimensions of the particle monitoring device 200. Alternatively, the deflecting electrode ELEC2 may have a straight input edge (see e.g. FIG. 10b).

Figure 11:
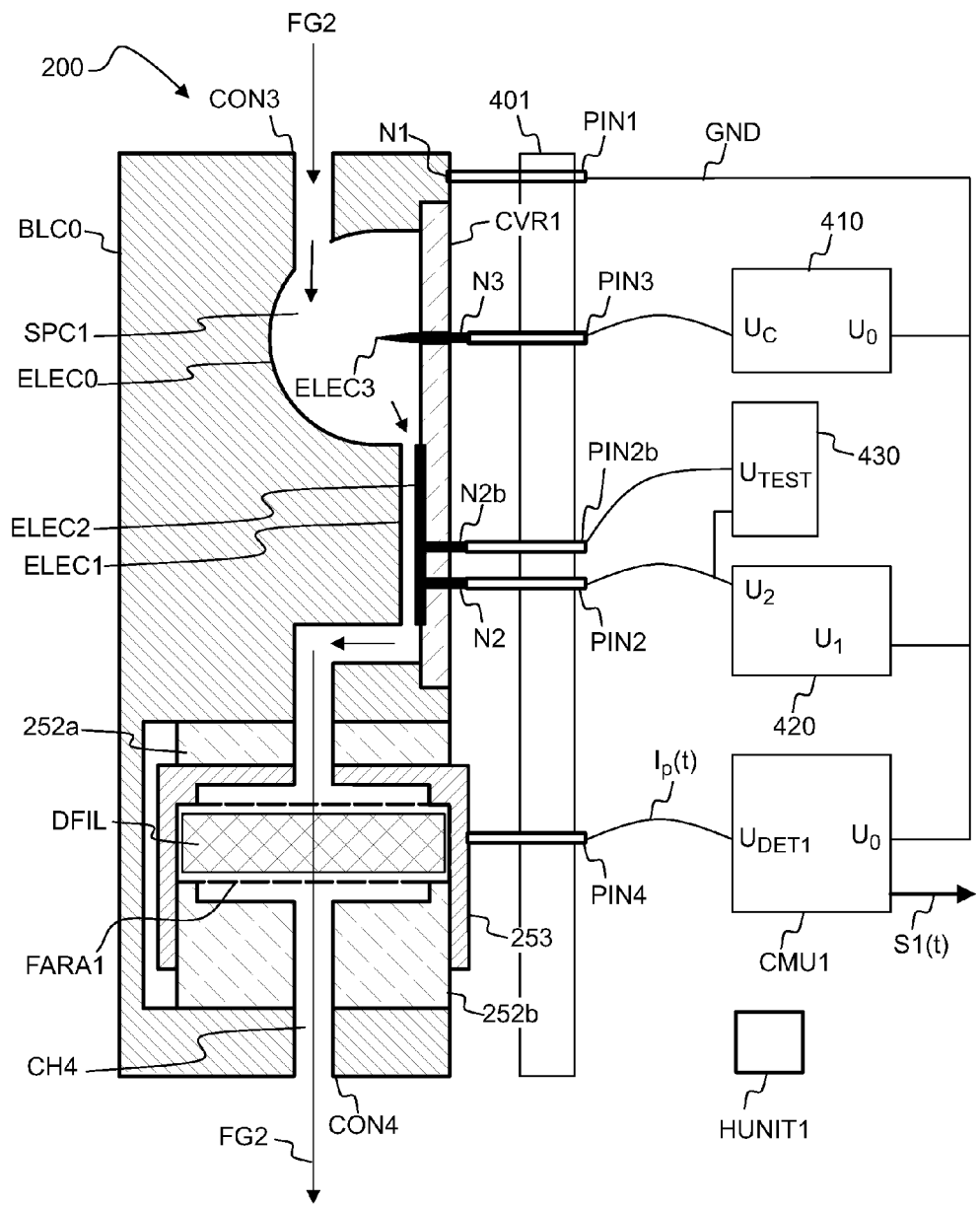
FIG. 11 shows, by way of example, electrical connections of the particle monitoring unit.

Referring to FIGS. 4 and 11, the particle monitoring device 200 may be electrically connected to a first voltage supply 410, to a second voltage supply 420, and to a current monitoring unit CMU1. The first voltage supply 410 may provide a voltage $U_C$, which may be applied to the corona electrode ELEC3 for generating the corona discharge. The first voltage supply 410 may provide a voltage $U_C$ with respect to the electrical ground GND. The electrical ground GND may have a voltage $U_0$. The counter electrode ELEC0 may be connected to the electrical ground GND. The body BLC0 may be connected to the electrical ground GND. The body BLC0 may be connected to the electrical ground GND e.g. by the connecting element PIN1.

The second voltage supply 420 may provide a voltage $U_1$ which may be applied to the first deflecting electrode ELEC1. The second voltage supply 420 may also provide a voltage $U_2$ which may be applied to the second deflecting electrode ELEC2. The voltage $U_1$ may be equal to the ground voltage $U_0$. The first deflecting electrode ELEC1 may be connected to the electrical ground GND e.g. via the conductive body BLC0.

The detector DET1 may provide the electric current $I_p(t)$. The current monitoring unit CMU1 may comprise an electrometer for measuring the electric current $I_p(t)$ obtained from the detector DET1. The current monitoring unit CMU1 may provide the monitoring signal $S1(t)$ by measuring the electric current $I_p(t)$.

The Faraday cage FARA1 of the detector DET1 may have a voltage $U_{DET1}$.

The voltage $U_C$ may be connected to the contact element N3 e.g. via the connecting element PIN3. The voltage $U_2$ may be connected to the deflecting electrode ELEC2 e.g. via the connecting element PIN2. The electric current signal $I_p(t)$ may be coupled to the current monitoring unit CMU1 e.g. via the connecting element PIN4. The connecting element PIN4 may be arranged to touch e.g. the side of the conductive shell 253 of the detector DET1. The measuring apparatus 500 may comprise e.g. a latch mechanism to fasten the monitoring device 200 to the frame 401 of a measuring apparatus. The monitoring device 200 may be fastened to the frame 401 so as to form a releasable connection between the elements PIN1 and N1, to form a releasable connection between the elements PIN2 and N2, to form a releasable connection between the elements PIN3 and N3, and/or to form a releasable connection between the element PIN4 and the detector DET1. The device 200 may be disconnected from the elements PIN1, PIN2, PIN3, PIN4 by opening the latch mechanism and by moving the monitoring device 200 away from the frame 401. The frame 401 may provide support for the elements PIN1, PIN2, PIN3, and/or PIN4.

The measuring apparatus may optionally comprise a proximity sensing unit 430 for checking whether the monitoring device 200 is properly attached to the frame 401. The measuring apparatus may optionally comprise a proximity sensing unit 430 for checking whether the electrical resistance of the electrical connection between the elements PIN2 and N2 is lower than a predetermined limit. For example, the apparatus 500 may be arranged to prevent operation of the high voltage supply 410 when the device 200 is not properly attached to the frame 401. In particular, the measuring apparatus may optionally comprise a proximity sensing unit 430 for checking whether the ion trap JTRAP1 of the monitoring device 200 is properly attached to the frame 401.

The monitoring device 200 may comprise one or more auxiliary contact elements N2b for measuring the electrical resistance of a connection formed between a contact element N2 of the monitoring device 200 and a connecting element PIN2. The proximity sensing unit 430 may be arranged to detect the proximity of the monitoring device 200 e.g. based on a voltage of a connecting element PIN2b. The proximity sensing unit 430 may measure e.g. the voltage $U_{TEST}$ of the contact element PIN2b. The contact element PIN2b may be arranged to contact a contact element N2b. The contact element N2b may be in galvanic connection with the element N2. If the voltage $U_{TEST}$ is equal to the voltage $U_2$, this may indicate that the element PIN2 is properly connected to the contact element N2. If the voltage $U_{TEST}$ is different from the voltage $U_2$, this may indicate that the element PIN2 is not properly connected to the contact element N2.

The device 200 may comprise a contact element (N2) for forming an electrical contact between a voltage supply (420) and an electrode (ELEC2), wherein the device 200 may further comprise an auxiliary contact element (N2b) for checking whether a proper electrical connection is formed between said voltage supply and said electrode.

The method may comprise:
  moving the monitoring device 200 away from the frame 401, attaching the monitoring device 200 back to the frame 401, and monitoring the voltage of an auxiliary connection element PIN2b in order to check whether a proper electrical connection is formed between a voltage supply and an electrode of the device 200.

The device 200 may optionally comprise a heating element HUNIT1 for heating the device 200 when the corona discharge DSR1 is not operating.

The device 200 may comprise a channel CH4 for guiding the particle-free gas flow FG2 from the detector DET1 to the pump PUMP2. The pump PUMP2 may be connected to the channel CH4 e.g. by a connector CON4.

The device 200 may be used for checking the validity of a gravimetric measurement result. Checking the validity of the gravimetric measurement result may improve the reliability and/or accuracy of an output result determined from one or more gravimetric measurement result. An output result may be obtained e.g. by averaging two or more valid measurement results. An output result may be determined from one or more gravimetric measurement results by rejecting invalid measurement results so that the invalid measurement results do not contribute to the output result. In particular, an output result may be determined from two or more gravimetric measurement results by rejecting one or more invalid measurement results so that the invalid measurement results do not contribute to the output result.

The gravimetric measurement result may mean the total mass $m_{tot}$ and/or the average concentration $C_{ave,tot}$ obtained by a gravimetric measurement. The total mass $m_{tot}$ may be determined by weighing the filter FIL1 after a particle collecting period $T_{tot}$. The average concentration $C_{ave,tot}$ may be subsequently calculated from the total mass $m_{tot}$.

A particle emission experiment may involve running the aerosol particle source SRC1 according to a test sequence during several hours. The particle source SRC1 may be e.g. an engine. The engine SRC1 may generate aerosol particles to the exhaust gas PG0. A gravimetric measurement result may be obtained by collecting aerosol particles of the exhaust gas PG0 to a first filter FIL1 during a first particle collecting period $T_{tot,1}$. Performing particle emission experiments may be expensive. A particle emission experiment may be interrupted if analysis of the monitor signal $S1(t)$ indicates already during the experiment that the experiment is likely to provide an invalid gravimetric measurement result. A particle emission experiment may be repeated if analysis of the monitor signal $S1(t)$ indicates that the experiment provides an invalid gravimetric measurement result. One or more additional experiments may be performed until at least one additional experiment provides a valid gravimetric measurement result. The method may comprise obtaining one or more additional gravimetric measurement results until the number of valid gravimetric measurement results is greater than or equal to a predetermined limit.

The collecting unit 100 of the apparatus 500 may comprise a first filter FIL1 during a first measurement time period $T_{tot,1}$. The first filter FIL1 may be replaced with a second filter FIL2 for obtaining a second gravimetric measurement result. The collecting unit 100 may comprise a second filter FIL2 during a second measurement time period $T_{tot,2}$.

The method may comprise:
collecting particles (P1) from the sampling point (POS0) to a first filter (FIL1) during a first measurement time period ($T_{tot,1}$), obtaining a first gravimetric measurement result ($m_{tot,1}$) by weighing the filter (FIL1) after the first measurement time period ($T_{tot,1}$), measuring the electric current signal $I_p(t)$ during the first measurement time period ($T_{tot,1}$), and classifying the first gravimetric measurement result ($m_{tot,1}$) as valid or invalid by analyzing the electric current signal $I_p(t)$ measured during the first measurement time period ($T_{tot,1}$).

The method may comprise:
collecting particles (P1) from the sampling point (POS0) to a second filter (FIL2) during a second measurement time period ($T_{tot,2}$), obtaining a second gravimetric measurement result ($m_{tot,2}$) by weighing the filter (FIL2) after the second measurement time period ($T_{tot,2}$), measuring the electric current signal $I_p(t)$ during the second measurement time period ($T_{tot,2}$), and classifying the second gravimetric measurement result ($m_{tot,2}$) as valid or invalid by analyzing the electric current signal $I_p(t)$ measured during the second measurement time period ($T_{tot,2}$).

A first group of gravimetric measurement results may comprise the first result ($m_{tot,1}$) and the second result ($m_{tot,2}$). The method may comprise determining an output result from one or more valid results of the first group. The invalid results may be omitted. The output result may be determined e.g. averaging the valid results. The output result may be determined e.g. by fitting a curve to the valid results. The method may comprise collecting particles from the sampling point POS0 during an additional measurement time period ($T_{tot,3}$) if the first result ($m_{tot,1}$) and the second result ($m_{tot,2}$) are invalid. The particles may be collected to a third filter FIL3 during the additional measurement time period ($T_{tot,3}$). A third gravimetric measurement result $m_{tot,3}$ may be obtained by weighing the filter FIL3 after the additional measurement time period ($T_{tot,3}$). During the time periods $T_{tot,1}$, $T_{tot,2}$, $T_{tot,3}$, the particles may be generated by the same particle source SRC1, and particles may be sampled from the same location POS0. To the first approximation, the size distribution and/or the composition of the particles may remain substantially similar during the different experiments even in a situation where the concentration of the particles may exhibit significant changes.

Analysis of the electric current signal $I_p(t)$ may comprise e.g. determining whether the average or integral of the electric current signal $I_p(t)$ measured during the first time period ($T_{tot,1}$) corresponds to the first gravimetric measurement result ($m_{tot,1}$).

A first integral SUM1 may be obtained by integrating the electric current $I_p(t)$ over the first measurement time period $T_{tot,1}$. A second integral SUM2 may be obtained by integrating the electric current $I_p(t)$ over the second measurement time period $T_{tot,2}$. The method may comprise checking whether The ratio SUM1/SUM2 corresponds to the ratio $m_{tot,1}/m_{tot,2}$. The first result $m_{tot,1}$ and/or the second result $m_{tot,2}$ may be determined to be invalid e.g. if the following condition is not fulfilled:

$$0.8 < \frac{m_{tot,1}/m_{tot,2}}{SUM1/SUM2} < 1.2 \tag{4}$$

A first experiment TEST1 may involve collecting the particles to a first filter FIL1 during a first measurement time period $T_{tot,1}$. A second experiment TEST2 may involve collecting the particles to a second filter FIL2 during a second measurement time period $T_{tot,2}$.

FIG. 12a shows, by way of example, a first integral SUM1 of the current over the first measurement time period $T_{tot,1}$, and a second integral SUM2 of the current over the second measurement time period $T_{tot,2}$. FIG. 12b shows, by way of example, the total mass $m_{tot,1}$ of particles collected during the time period $T_{tot,1}$, and the total mass $m_{tot,2}$ of particles collected during the time period $T_{tot,2}$. In the example shown in FIGS. 12a and 12b, the ratio SUM1/SUM2 substantially corresponds to the ratio $m_{tot,1}/m_{tot,2}$. This may indicate that the results $m_{tot,1}$ and $m_{tot,2}$ are valid.

FIG. 13a shows, by way of example, a first integral SUM1 of the current over the first measurement time period $T_{tot,1}$, and a second integral SUM2 of the current over the second measurement time period $T_{tot,2}$. FIG. 13b shows, by way of example, the total mass $m_{tot,1}$ of particles collected during the time period $T_{tot,1}$, and the total mass $m_{tot,2}$ of particles collected during the time period $T_{tot,2}$. In the example shown in FIGS. 13a and 13b, the ratio SUM1/SUM2 substantially deviates from the ratio $m_{tot,1}$, $m_{tot,2}$. This may indicate that the gravimetric measurement result $m_{tot,1}$ and/or $m_{tot,2}$ is invalid. The method may comprise performing at least one additional experiment TEST3 when at least one of the results $m_{tot,1}$ and/or $m_{tot,2}$ of the earlier experiments TEST1, TEST2 is determined to be invalid. SUM3 denotes a third integral SUM3 of the current over an additional measurement time period $T_{tot,3}$. The symbol $m_{tot,3}$ denotes the total mass of particles collected to a filter FIL3 during the additional time period $T_{tot,3}$. In the example shown in FIGS. 13a and 13b, the ratio SUM2/SUM3 substantially corresponds to the ratio $m_{tot,2}/m_{tot,3}$, and the result $m_{tot,2}$ and/or $m_{tot,3}$ may be determined to be valid. Comparison of the integrals SUM1, SUM2, SUM3 with the results $m_{tot,1}$, $m_{tot,2}$, $m_{tot,3}$ may indicate that the result $m_{tot,1}$ is invalid, and that the results $m_{tot,2}$ and $m_{tot,3}$ are valid.

$I_{ave,1}$ may denote the average value of the current signal $I_p(t)$ during the first measurement time period $T_{tot,1}$. $I_{ave,2}$ may denote the average value of the current signal $I_p(t)$ during the first measurement time period $T_{tot,1}$. $C_1$ may denote the average concentration determined from the total mass $M_{tot,1}$. $C_2$ may denote the average concentration determined from the total mass $m_{tot,2}$. The first average concentration $C_1$ and/or the second concentration $C_2$ may be determined to be invalid e.g. if the following condition is not fulfilled:

$$0.8 < \frac{C_1/C_2}{I_{ave,1}/I_{ave,2}} < 1.2 \quad (5)$$

Analysis of the electric current signal $I_p(t)$ may comprise comparing the monitor signal S1(t) with a process indicator signal P(t). The process indicator signal P(t) may indicate an operating parameter of the particle source SRC. For example, the process indicator signal P(t) may be indicative of fuel flow rate, input air flow rate to an engine, rotation speed of an engine, torque generated by an engine, output power of an engine, rotation speed of a dynamometer, torque of a dynamometer, power coupled from an engine to a dynamometer, operating temperature of an engine, operating temperature of a cylinder of an engine, operating temperature of a catalytic converter, operating temperature of an exhaust gas filter, operating temperature of a process, gas pedal setting, valve timing of an engine, fuel feeding pressure, or flow rate of an additive.

The monitor signal S1(t) may be compared with the process indicator signal P(t) in order to determine whether a change of an operating parameter of the aerosol particle source SRC1 corresponds to a change of the monitor signal S1(t). The monitor signal S1(t) may be compared with the process indicator signal P(t) in order to determine whether a change of an operating parameter of the source SRC1 temporally coincides with a change of the monitor signal S1(t). The monitor signal S1(t) may be compared with the process indicator signal P(t) in order to determine whether the monitor signal S1(t) correlates with the process indicator signal P(t). The method may comprise calculating a cross-correlation between the electric current signal $I_p(t)$ and the first process indicator signal P(t), and checking whether the cross-correlation is higher than a predetermined value.

The gravimetric measurement result ($m_{tot,1}$) may be determined to be invalid if the degree of correlation between the monitor signal S1(t) and the process indicator signal P(t) is below a predetermined limit.

Figure 14A:
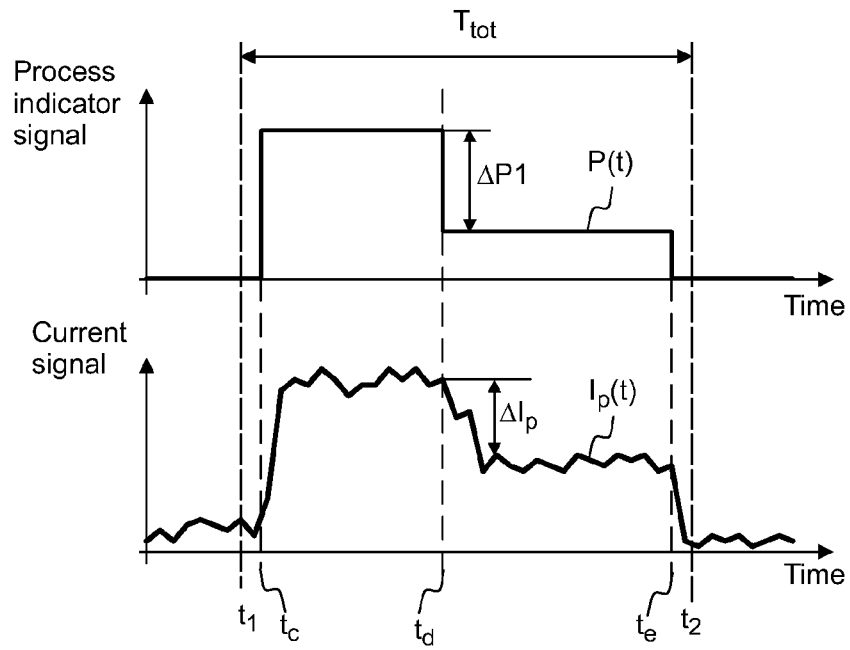
FIG. 14a shows, by way of example, a current signal which correlates with a process indicator signal.

FIG. 14a shows, by way of example, temporal evolution of a process indicator signal P(t) during an experiment, and the temporal evolution of the current signal $I_p(t)$ measured during said experiment. A particle collecting period $T_{tot}$ may start at the time $t_1$, and stop at the time $t_2$. The process indicator signal P(t) may exhibit a change ΔP1 at the time $t_d$. The process indicator signal P(t) may indicate e.g. the fuel feed rate or output power of an internal combustion engine SRC1. The engine may be started e.g. at a time $t_0$, and stopped at the time $t_0$. The current signal may exhibit a change ΔI, which may temporally coincide with the change ΔP1 of the process indicator signal P(t). The current signal $I_p(t)$ may be determined to correlate with the process indicator signal P(t) in the example shown in FIG. 14a.

In an embodiment, one or more process indicator signals P(t) may indicate that the particle concentration should be substantially constant during the first measurement time period ($T_{tot,1}$). In that case, the gravimetric measurement result ($m_{tot,1}$) may be determined to be invalid if the current signal $I_p(t)$ exhibits significant deviations from the average value $I_{ave,1}$ of the current signal $I_p(t)$.

The symbol $I'_p(t)$ may denote a smoothed signal obtained by low-pass filtering the current signal $I_p(t)$. The smoothed signal $I'_p(t)$ may be formed from the current signal $I_p(t)$ e.g. by using a cut-off frequency 0.10 Hz. The smoothed signal $I'_p(t)$ may be formed from the current signal $I_p(t)$ such that the smoothed signal $I'_p(t)$ does not comprise spectral components whose frequency is lower than 0.1 Hz. The method may comprise determining whether the smoothed signal $I'_p(t)$ deviates more than 20% from the average value of the current signal at any time t during the first measurement time period $T_{tot,1}$. The gravimetric measurement result ($m_{tot,1}$) may be determined to be invalid e.g. if the following condition is satisfied for any time t during the time period $T_{tot,1}$.

$$\frac{|I'_p(t) - I_{ave,1}|}{I_{ave,1}} > 0.20 \quad (6)$$

$I_{ave,1}$ denotes the average value of the electric current signal $I_p(t)$ during the first measurement time period ($T_{tot,1}$).

Figure 14B:
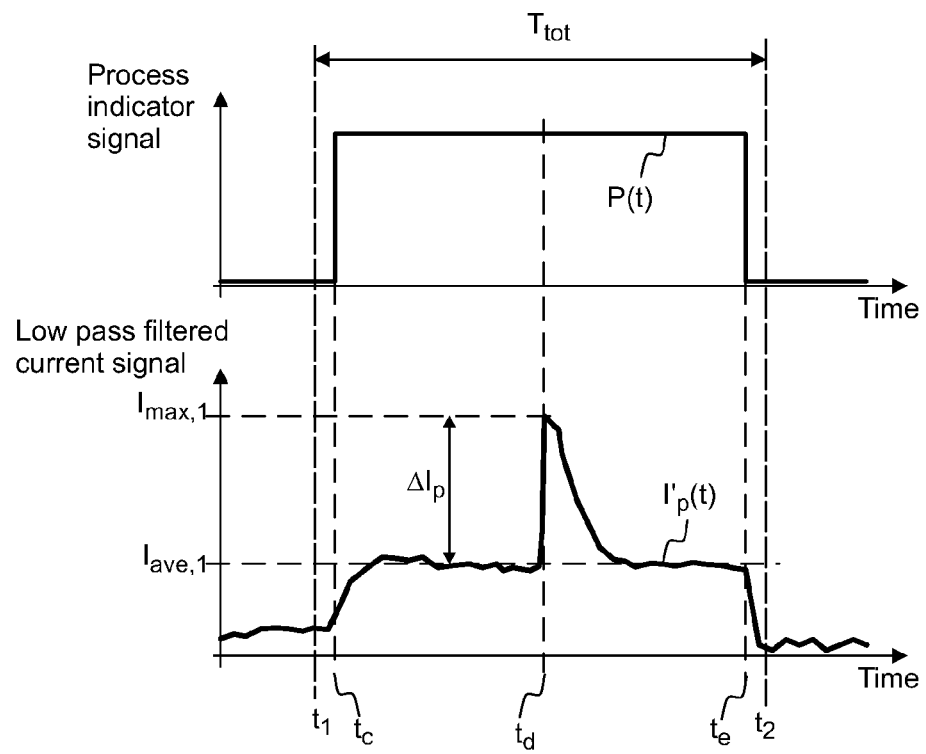
FIG. 14b shows, by way of example, a current signal, which exhibits anomalous behavior.

FIG. 14b shows, by way of example, a situation where low pass filtered current signal $I'_p(t)$ exhibits an anomalous change $\Delta I_p$, which does not correspond to the process indicator signal P(t). The anomalous change $\Delta I_p$ may take place at the time $t_d$. In this example, the process indicator signal P(t) may be substantially constant during the time period from a first time $t_c$ to a second time $t_e$. Said time period may comprise the time $t_d$. A gravimetric measurement result $m_{tot,1}$ may be obtained by collecting particles to a filter FIL1 during the time period $T_{tot}$ from $t_1$ to $t_2$, and by weighing the filter FIL1 after the time period $T_{tot}$. The result $m_{tot,1}$ may be determined to be valid e.g. if all significant changes ($\Delta I_p$) of the current signal $I_p(t)$ temporally coincide with changes of at least one process indicator signal obtained from the particle source SRC1. The result $m_{tot,1}$ may be determined to be invalid e.g. if all process indicator signals obtained from the particle source SRC1 are substantially constant during the time period which comprises the time $t_d$.

If the change $\Delta I_p$ does not correlate with any process indicator signal P(t), this may be an indication that the change $\Delta I_p$ is caused by a random event. The change $\Delta I_p$ may be caused e.g. when particles deposited on the surface of the exhaust gas duct DUC1 are suddenly released back to the exhaust gas flow PG0. Although the change $\Delta I_p$ may be caused by a true increase of the particle concentration, said change $\Delta I_p$ may be caused by a random event, which may lead to erroneous conclusions if the result $m_{tot,1}$ would be used e.g. as a data point for curve fitting. Analysis of the electric current $I_p(t)$ may indicate that an anomalous event has occurred. The apparatus 500 may be arranged to provide an indication to the user that an anomalous event has been detected.

A gravimetric measurement result may be subjected to one or more tests. The tests may include e.g. the checking the degree of correlation between the current signal $I_p(t)$ and the process indicator signal P(t), checking the condition of equation (5), and/or checking the condition of equation (6). The gravimetric measurement result may be determined to be valid e.g. if all said tests indicate that the gravimetric measurement result is valid. A gravimetric measurement result may be determined to be valid if the result is classified to be valid in all said tests.

In an embodiment, the monitoring device 200 may also be arranged to monitor aerosol particle concentration of an input flow FG0 without using the distributor 300 and the particle collecting unit 100. The input flow FG0 may be directly guided to the monitoring device 200. The monitoring device 200 may be manufactured, stored, and/or provided to a user, which may subsequently use the monitoring device 200 for continuous monitoring of aerosol particle concentration. The monitoring device 200 may comprise e.g. the substantially hemispherical charging space SPC1 as shown e.g. in FIGS. 10a-11.

Various aspects of the invention are illustrated by the following examples:

Example 1

A particle measuring apparatus (500), comprising:
a distributor unit (300) arranged to provide a first partial flow (FG1) and a second partial flow (FG2) by separating the second partial flow (FG2) from an input flow (FG0),
a particle collecting unit (100) to collect particles (P1) from the first partial flow (FG1) by using a first filter (FIL1), and
a particle monitoring unit (200) to form charged particles (P2) by charging particles (P1) carried by the second partial flow (FG2), and to provide an electric current ($I_p(t)$) by collecting the charged particles (P2).

Example 2

The apparatus (500) of example 1, comprising a charging unit (CUNIT1) to charge particles (P1) of the second partial flow (FG2) by a corona discharge (DSR1).

Example 3

The apparatus (500) of example 1 or 2, comprising a particle detector (DET1) to collect the charged particles (P2), wherein the particle detector (DET1) comprises a filter (DFIL) enclosed in a Faraday cage (FARA1).

Example 4

The apparatus (500) according to any of the examples 1 to 3, comprising an ion trap (JTRAP) to remove ions (J1) from the second partial flow (FG2).

Example 5

The apparatus (500) according to any of the examples 1 to 4, comprising a pump (PUMP2) to draw the second partial flow (FG2) through the particle monitoring unit (200).

Example 6

The apparatus (500) according to any of the examples 1 to 5, wherein the apparatus (500) comprises a flow sensor (SEN1) to monitor the flow rate ($Q_1$) of the first partial flow (FG1), and wherein the apparatus (500) is arranged to start the second partial flow (FG2) based on the flow rate ($Q_1$) of the first partial flow (FG1).

Example 7

The apparatus (500) according to any of the examples 1 to 6, wherein the apparatus (500) comprises a primary duct (310) for guiding the first partial flow (FG1) to the first filter (FIL1), wherein the primary duct (310) comprises a straight portion (POR1) and a diverging portion (POR2).

Example 8

The apparatus (500) according to any of the examples 1 to 7, wherein the particle monitoring unit (200) comprises:
a counter-electrode (ELEC0) having a substantially hemispherical inner portion to define a charging space (SPC1),
an inlet channel (CH1) for guiding aerosol particles (P1) into the charging space (SPC1),
a corona electrode (ELEC3) to form charged particles (P2) from the aerosol particles (P1) by generating a corona discharge in the charging space (SPC1), and
an outlet channel (CH2) for guiding charged particles (P2) from the charging space (SPC1).

Example 9

The apparatus (500) according to any of the examples 1 to 8, wherein the particle monitoring unit (200) comprises:
a voltage supply (410) to provide operating voltage ($U_C$) to a corona electrode (ELEC3), a current monitoring unit (CMU1) to measure the electric current ($I_p(t)$), and a heating unit (HUNIT1) to heat the current monitoring unit (CMU1), wherein the apparatus (500) is arranged to control the heating unit (HUNIT1) based on operating status of the voltage supply (410).

Example 10

The apparatus (500) according to any of the examples 1 to 9, comprising:
a frame (401), and
a proximity sensing unit (430) to check whether the particle monitoring unit (200) is properly attached to the frame (401).

Example 11

A method for measuring aerosol particles (P1), the method comprising:
providing a first partial flow (FG1) and a second partial flow (FG2) by separating the second partial flow (FG2) from an input flow (FG0) by using a distributor unit (300),
collecting particles (P1) from the first partial flow (FG1) by using a filter (FIL1),
forming charged particles (P2) by charging particles (P1) carried by the second partial flow (FG2), and
providing an electric current ($I_p(t)$) by collecting the charged particles (P2).

Example 12

The method of example 11 comprising starting the second partial flow (FG2) based on the flow rate ($Q_1$) of the first partial flow (FG1).

Example 13

The method of example 11 or 12 comprising stopping the second partial flow (FG2) based on the flow rate ($Q_1$) of the first partial flow (FG1).

14. The method according to any of the examples 11 to 13, comprising providing the input flow (FG0) by sampling from diluted exhaust gas (PG0) of an internal combustion engine.

Example 15

The method according to any of the examples 11 to 14, comprising:
collecting particles (P1) by guiding the first partial flow (FG1) through the first filter (FIL1) during a first measurement time period ($T_{tot,1}$), and
obtaining a first gravimetric measurement result ($m_{tot,1}$) by weighing the first filter (FIL1) after the first measurement time period ($T_{tot,1}$).

Example 16

The method of example 15, comprising:
measuring the electric current signal $I_p(t)$ during the first measurement time period ($T_{tot,1}$), and
classifying the first gravimetric measurement result ($m_{tot,1}$) as valid or invalid by analyzing the electric current signal $I_p(t)$ measured during the first measurement time period ($T_{tot,1}$).

Example 17

The method of example 16, comprising:
collecting particles (P1) by guiding the first partial flow (FG1) to a second filter (FIL2) during a second measurement time period ($T_{tot,2}$),
obtaining a second gravimetric measurement result ($m_{tot,2}$) by weighing the filter (FIL2) after the second measurement time period ($T_{tot,2}$),
measuring the electric current signal $I_p(t)$ during the second measurement time period ($T_{tot,2}$), and
classifying the first gravimetric measurement result ($m_{tot,1}$) as valid or invalid by determining whether a first ratio ($m_{tot,1}/m_{tot,2}$) of the first gravimetric measurement result ($m_{tot,1}$) to the second gravimetric measurement result ($m_{tot,2}$) substantially corresponds to a second ratio (SUM1/SUM2) of a first integral (SUM1) of the electric current signal $I_p(t)$ over the first measurement time period ($T_{tot,1}$) to a second integral (SUM2) of the electric current signal $I_p(t)$ over the second measurement time period ($T_{tot,2}$).

Example 18

The method according to any of the examples 11 to 17, comprising:
operating an engine (SRC1),
collecting particles (P1) of an exhaust gas (PG0) of the engine (SRC1) by guiding the first partial flow (FG1) to the first filter (FIL1) during a first measurement period ($T_{tot,1}$),
measuring the electric current ($I_p(t)$) during the first measurement period ($T_{tot,1}$),
obtaining a process indicator signal (P(t)) indicative of an operating parameter of the engine (SRC1),
obtaining a first gravimetric measurement result ($m_{tot,1}$) by weighing the first filter (FIL1) after the first measurement time period ($T_{tot,1}$), and
classifying the first gravimetric measurement result ($m_{tot,1}$) as valid or invalid by determining whether the electric current ($I_p(t)$) measured during the first measurement period ($T_{tot,1}$) correlates with the process indicator signal (P(t)).

Example 19

The method according to any of the examples 11 to 18, comprising:
guiding the particles (P1) of the second partial flow (FG2) into a charging space (SPC1), which is located between a corona electrode (ELEC3) and a counter-electrode (ELEC0), which has a substantially hemispherical inner portion, and
forming the charged particles (P2) by charging the particles (P1) of the second partial flow (FG2) in the charging space (SPC1).

Example 20

The method according to any of the examples 11 to 19, comprising:
forming charged particles (P2) by a corona discharge (DSR1),
measuring the electric current ($I_p(t)$) by using a current monitoring unit (CMU1), and controlling heating of the current monitoring unit (CMU1) based on operating status of the corona discharge (DSR1).

For the person skilled in the art, it will be clear that modifications and variations of the devices and the methods according to the present invention are perceivable. The figures are schematic. The particular embodiments described above with reference to the accompanying drawings are illustrative only and not meant to limit the scope of the invention, which is defined by the appended claims.

The invention claimed is:

1. A particle measuring apparatus, comprising:
a distributor unit arranged to provide a first partial flow and a second partial flow by separating the second partial flow from an input flow,
a particle collecting unit to collect particles from the first partial flow by using a first filter,
a flow sensor to monitor the flow rate of the first partial flow,
a pump to draw the second partial flow through the particle monitoring unit, and
a particle monitoring unit to form charged particles by charging particles carried by the second partial flow, and to provide an electric current by collecting the charged particles,
wherein the apparatus is arranged to start the second partial flow based on the flow rate of the first partial flow.

2. The apparatus of claim 1, comprising a charging unit to charge particles of the second partial flow by a corona discharge.

3. The apparatus of claim 1, comprising a particle detector to collect the charged particles, wherein the particle detector comprises a monitoring filter enclosed in a Faraday cage.

4. The apparatus of claim 1, comprising an ion trap to remove ions from the second partial flow.

5. The apparatus of claim 1, wherein the apparatus comprises a primary duct for guiding the first partial flow to the first filter, wherein the primary duct comprises a straight portion and a diverging portion.

6. The apparatus of claim 1, wherein the particle monitoring unit comprises:
a counter-electrode having a substantially hemispherical inner portion to define a charging space,
an inlet channel for guiding aerosol particles into the charging space,
a corona electrode to form charged particles from the aerosol particles by generating a corona discharge in the charging space, and
an outlet channel for guiding charged particles from the charging space.

7. The apparatus of claim 1, comprising:
a voltage supply to provide operating voltage to a corona electrode,
a current monitoring unit to measure the electric current, and
a heating unit to heat the current monitoring unit,
wherein the apparatus is arranged to control the heating unit based on operating status of the voltage supply.

8. The apparatus of claim 1, comprising:
a frame, and
a proximity sensing unit to check whether the particle monitoring unit is properly attached to the frame.

9. A method for measuring aerosol particles, the method comprising:
providing a first partial flow and a second partial flow by separating the second partial flow from an input flow by using a distributor unit,
starting the second partial flow based on the flow rate of the first partial flow,
collecting particles from the first partial flow by using a first filter,
forming charged particles by charging particles carried by the second partial flow, and
providing an electric current by collecting the charged particles.

10. The method of claim 9 comprising stopping the second partial flow based on the flow rate of the first partial flow.

11. The method of claim 9, comprising providing the input flow by sampling from diluted exhaust gas of an internal combustion engine.

12. The method of claim 9, comprising:
collecting particles by guiding the first partial flow through the first filter during a first measurement time period, and
obtaining a first gravimetric measurement result by weighing the first filter after the first measurement time period.

13. The method of claim 12, comprising:
measuring the electric current during the first measurement time period, and
classifying the first gravimetric measurement result as valid or invalid by analyzing the electric current measured during the first measurement time period.

14. The method of claim 13, comprising:
collecting particles by guiding the first partial flow to a second filter during a second measurement time period,
obtaining a second gravimetric measurement result by weighing the filter after the second measurement time period,
measuring the electric current during the second measurement time period, and
classifying the first gravimetric measurement result as valid or invalid by determining whether a first ratio of the first gravimetric measurement result to the second gravimetric measurement result substantially corresponds to a second ratio of a first integral of the electric current over the first measurement time period to a second integral of the electric current over the second measurement time period.

15. The method of claim 9, comprising:
operating an engine,
collecting particles of an exhaust gas of the engine by guiding the first partial flow to the first filter during a first measurement period,
measuring the electric current during the first measurement period,
obtaining a process indicator signal indicative of an operating parameter of the engine,
obtaining a first gravimetric measurement result by weighing the first filter after the first measurement time period, and
classifying the first gravimetric measurement result as valid or invalid by determining whether the electric current measured during the first measurement period correlates with the process indicator signal.

16. The method of claim 11, comprising:
guiding the particles of the second partial flow into a charging space, which is located between a corona electrode and a counter-electrode, which has a substantially hemispherical inner portion, and forming the charged particles by charging the particles of the second partial flow in the charging space.

17. A method for measuring aerosol particles, the method comprising:
providing a first partial flow and a second partial flow by separating the second partial flow from an input flow by using a distributor unit,
stopping the second partial flow based on the flow rate of the first partial flow,
collecting particles from the first partial flow by using a first filter,
forming charged particles by charging particles carried by the second partial flow, and
providing an electric current by collecting the charged particles.

18. The method of claim 11, comprising:
forming charged particles by a corona discharge,
measuring the electric current by using a current monitoring unit, and
controlling heating of the current monitoring unit based on operating status of the corona discharge.

* * * * *